(12) United States Patent
Chong et al.

(10) Patent No.: US 12,297,230 B2
(45) Date of Patent: *May 13, 2025

(54) SYNTHETIC SYSTEM FOR TUNABLE THRESHOLDING OF PROTEIN SIGNALS

(71) Applicant: California Institute of Technology, Pasadena, CA (US)

(72) Inventors: Lucy S. Chong, Pasadena, CA (US); Ronghui Zhu, Pasadena, CA (US); Xiaofei Ge, Beijing (CN); Michael B. Elowitz, Pasadena, CA (US); Mark W. Budde, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,102

(22) Filed: May 11, 2023

(65) Prior Publication Data

US 2024/0101606 A1  Mar. 28, 2024

Related U.S. Application Data

(63) Continuation of application No. 16/738,664, filed on Jan. 9, 2020, now Pat. No. 11,667,676.

(60) Provisional application No. 62/790,553, filed on Jan. 10, 2019.

(51) Int. Cl.
*A61K 38/00* (2006.01)
*C07K 14/00* (2006.01)
*C12N 9/22* (2006.01)

(52) U.S. Cl.
CPC ............. *C07K 14/001* (2013.01); *C12N 9/22* (2013.01)

(58) Field of Classification Search
CPC ..... A61P 35/00; C07K 14/001; C07K 14/245; C07K 19/00; C07K 2319/70; C07K 2319/81; C12N 15/63; C12N 2310/20; C12N 9/22; C12N 9/503
See application file for complete search history.

(56) References Cited

U.S. PATENT DOCUMENTS

| | | |
|---|---|---|
| 5,739,002 A | 4/1998 | De Francesco et al. |
| 6,005,079 A | 12/1999 | Casterman et al. |
| 6,348,584 B1 | 2/2002 | Hodgson et al. |
| 6,673,901 B2 | 1/2004 | Koide |
| 6,856,914 B1 | 2/2005 | Pelech |
| 6,884,870 B2 | 4/2005 | Hav et al. |
| 8,394,604 B2 | 3/2013 | Liu et al. |
| 10,899,823 B2 | 1/2021 | Gao et al. |
| 11,453,893 B2 | 9/2022 | Gao et al. |
| 11,542,305 B2 | 1/2023 | Gao et al. |
| 11,667,676 B2 * | 6/2023 | Chong ............... C12N 9/22 530/333 |
| 2002/0132327 A1 | 9/2002 | Hay et al. |
| 2005/0271647 A1 | 12/2005 | Baltimore et al. |
| 2008/0227750 A1 | 9/2008 | Dennis et al. |
| 2009/0162341 A1 | 6/2009 | Foster et al. |
| 2013/0230863 A1 | 9/2013 | Tang et al. |
| 2015/0315570 A1 | 11/2015 | Zhao et al. |
| 2016/0223529 A1 | 8/2016 | Stein et al. |
| 2017/0315114 A1 | 11/2017 | Stein et al. |
| 2018/0118818 A1 | 5/2018 | Tang et al. |
| 2019/0248873 A1 | 8/2019 | Gao et al. |
| 2021/0238570 A1 | 8/2021 | Gao et al. |

FOREIGN PATENT DOCUMENTS

| | | |
|---|---|---|
| WO | WO1994004678 | 3/1994 |
| WO | WO1994025591 | 11/1994 |
| WO | WO2014040129 | 3/2014 |
| WO | WO2015017214 | 2/2015 |
| WO | WO2015164594 | 10/2015 |
| WO | WO2018069782 | 4/2018 |
| WO | WO2019147478 | 8/2019 |

OTHER PUBLICATIONS

Adams et al., "Overview and analysis of the polyprotein cleavage sites in the family Potyviridae," Molecular Plant Pathology 2005, 6(4), 471-487.
Angelici et al., "Synthetic Biology Platform for Sensing and Integrating Endogenous Transcriptional Inputs in Mammalian Cells," Cell Reports 2016, 16, 2525-2537.
Aronheim et al., "Membrane Targeting of the Nucleotide Exchange Factor Sos Is Sufficient for Activating the Ras Signaling Pathway," Cell 1994, 78, 949-961.
Auslander et al., "Programmable single-cell mammalian biocomputers," Nature 2012, 487, 123-127.
Banaszynski et al., "A Rapid, Reversible, and Tunable Method to Regulate Protein Function in Living Cells Using Synthetic Small Molecules," Cell 2006, 126, 995-1004.
Barnea et al., "The genetic design of signaling cascades to record receptor activation," PNAS 2008, 105(1), 64-69.
Barrett et al., "Chimeric Antigen Receptor Therapy for Cancer," Annual Review of Medicine 2014, 65, 333-347.
Bartenschlager et al., "The NS3/4A proteinase of the hepatitis C virus: unravelling structure and function of an unusual enzyme and a prime target for antiviral therapy," Journal of Viral Hepatitis 1999, 6, 165-181.
Basu et al., "A synthetic multicellular system for programmed pattern formation," Nature 2005, 434, 1130-1134.
Basu et al., "Spatiotemporal control of gene expression with pulse-generating networks," PNAS 2004, 101(17), 6355-6360.
Bintu et al., "Dynamics of epigenetic regulation at the single-cell level," Science 2016, 351(6274), 720-724.

(Continued)

*Primary Examiner* — Aradhana Sasan
*Assistant Examiner* — Mercy H Sabila
(74) *Attorney, Agent, or Firm* — Dickinson Wright PLLC

(57) ABSTRACT

Disclosed herein include methods, compositions, and kits suitable for use in thresholding of protein signals. There are provided, in some embodiments, synthetic protein circuits that respond to inputs only above or below a certain threshold concentration. In some embodiments, the threshold value itself is tunable. Methods of treating a disease or disorder characterized by aberrant signaling are provided in some embodiments.

20 Claims, 17 Drawing Sheets
Specification includes a Sequence Listing.

(56) References Cited

OTHER PUBLICATIONS

Boerger et al., "Retroviral vectors preloaded with a viral receptor-ligand bridge protein are targeted to specific cell types," PNAS 1999, 96, 9867-9872.
Bonnet et al., "Amplifying Genetic Logic Gates," Science 2013, 340, 599-602.
Budihardjo et al., "Biochemical Pathways of Caspase Activation During Apoptosis," Annual Review of Cellular Development and Biology 1999, 15, 269-290.
Butko et al., "Fluorescent and photo-oxidizing TimeSTAMP tags track protein fates in light and electron microscopy," Nature Neuroscience 2012, 15(12), 1742-1751.
Camacho-Soto et al., "Ligand-Gated Split-Kinases," Journal of the American Chemical Society 2014, 136, 3995-4002.
Camacho-Soto et al., "Small Molecule Gated Split-Tyrosine Phosphatases and Orthogonal Split-Tyrosine Kinases," Journal of the American Chemical Society 2014, 136, 17078-17086.
Carrington et al., "A viral cleavage site cassette: Identification of amino acid sequences required for tobacco etch virus polyprotein processing," PNAS 1988, 85, 3391-3395.
Chen et al., "Predicting PDZ domain-peptide interactions from primary sequences," Nature Biotechnology 2008, 26(9), 1041-1045.
Choi et al., "Selective viral vector transduction of ErbB4 expressing cortical interneurons in vivo with a viral receptor-ligand bridge protein," PNAS 2010, 107(38), 16703-16708.
Chung et al., "Tunable and reversible drug control of protein production via a self-excising degron," Nature Chemical Biology 2015, 11, 713-720.
Corrected Notice of Allowance dated Aug. 31, 2022 in U.S. Appl. No. 16/556,063.
Corrected Notice of Allowance dated Jun. 29, 2022 in U.S. Appl. No. 16/555,604.
Cox et al., "Drugging the undruggable Ras: mission possible?," Nature Reviews Drug Discovery 2014, 13(11), 828-851.
Dagliyan et al., "Computational design of chemogenetic and optogenetic split proteins," Nature Communications, 9(4042), 1-8, (2018).
Daringer et al., "Modular Extracellular Sensor Architecture for Engineering Mammalian Cell-based Devices," ACS Synthetic Biology 2014, 3, 892-902.
De Felipe et al., "Targeting of Proteins Derived from Self-Processing Polyproteins Containing Multiple Signal Sequences," Traffic 2004, 5, 616-626.
De Felipe, "Skipping the co-expression problem: the new 2A "Chysel" technology," Genetic Vaccines and Therapy 2004, 2(13).
Dissing et al., "Autoproteolysis and feedback in a protease cascade directing *Drosophila* dorsal-ventral cell fate," The EMBO Journal 2001, 20(10), 2387-2393.
Downward, "Targeting RAS Signaling Pathways in Cancer Therapy," Nature Publishing Group 2003, 3, 11-22.
Dueber et al., "Reprogramming Control of an Allosteric Signaling Switch Through Modular Recombination," Science 2003, 301, 1904-1908.
Elowitz et al., "A synthetic oscillatory network of transcriptional regulators," Nature 2000, 403, 335- 338.
Extended European Search Report dated Jun. 15, 2022 in European Patent Application No. 19854896.8.
Fernandez-Rodriguez et al., "Post-translational control of genetic circuits using Potyvirus proteases," Nucleic Acids Research 2016, 44(13), 6493-6502.
Ferrell et al., "Ultrasensitivity Part II: Multisite phosphorylation, stoichiometric inhibitors, and positive feedback," Trends in Biochemical Sciences 2014, 39(11), 556-569.
Fink et al., "Design of fast proteolysis-based signaling and logic circuits in mammalian cells," Nature Chemical Biology 2018, 15, 115-122.
Gao et al., "Programmable protein circuits in living cells," Science 2018, 361, 1252-1258.
Gardner et al., "Construction of a genetic toggle switch in Escherichia coli," Nature, 403, 339-342.

Ghabrial et al., "Molecular genetic analyses of the soybean mosaic virus NIa proteinase," Journal of General Virology 1990, 71, 1921-1927.
Ghosh et al., "Antiparallel Leucine Zipper-Directed Protein Reassembly: Application to the Green Fluorescent Protein," Journal of the American Chemical Society 2000, 122, 5658-5659.
Gramespacher et al., "Intein Zymogens: Conditional Assembly and Splicing of Split Inteins via Targeted Proteolysis," Journal of the American Chemical Society 2017, 139, 8074-8077.
Gray et al., "Activation of Specific Apoptotic Caspases with an Engineered Small Molecule-Activated Protease," Cell 2010, 142(4), 637-646.
Greber et al., "An engineered mammalian band-pass network," Nucleic Acids Research 2010, 38(18), e174.
Griesbeck et al., "Reducing the Environmental Sensitivity of Yellow Fluorescent Protein," The Journal of Biological Chemistry 2001, 276(31), 29188-29194. doi:10.1074/jbc.M102815200.
Hancock et al., "A CAAX or a CAAL motif and a second signal are sufficient for plasma membrane targeting of ras proteins," The EMBO Journal 1991, 10(13), 4033-4039.
Hart et al., "The Utility of Paradoxical Components in Biological Circuits," Molecular Cell 2013, 49, 213-221.
Herrmann et al., "Quantitative Analysis of the Complex between p21ras and the Ras-binding Domain of the Human Raf-1 Protein Kinase," Journal of Biological Chemistry 1995, 270(7), 2901-2905.
Holt, Brandon Alexander, and Gabriel A. Kwong. "Protease circuits for processing biological information." *Nature communications* 11.1 (2020): 5021.
Howard et al., "Redirecting tyrosine kinase signaling to an apoptotic caspase pathway through chimeric adaptor proteins," PNAS 2003, 100(20), 11267-11272.
International Search Report and Written Opinion dated Aug. 12, 2019 in PCT Patent Application PCT/US2019/014078.
International Search Report and Written Opinion dated Dec. 19, 2019 in PCT Patent Application PCT/US2019/048914.
International Search Report and Written Opinion dated May 7, 2020 in PCT Patent Application PCT/US2020/012928.
Iwamoto et al., "A General Chemical Method to Regulate Protein Stability in the Mammalian Central Nervous System," Chemistry & Biology 2010, 17, 981-988.
Jacobs et al., "StaPLs: versatile genetically encoded modules for engineering drug-inducible proteins," Nature Methods 2018, 15(7), 523-526.
Khalil et al., "A Synthetic Biology Framework for Programming Eukaryotic Transcription Functions," Cell 2012, 150, 647-658.
Kim et al., "Time-gated detection of protein-protein interactions with transcriptional readout," eLife 2017, 6, e30233.
Kipniss et al., "Engineering cell sensing and responses using a GPCR-coupled CRISPR-Cas system," Nature Communications 2017, 8, 2212.
Koch-Nolte et al., "Single domain antibodies from llama effectively and specifically block T cell ecto-ADP-ribosyltransferase ART2.2 in vivo," The FASEB Journal 2007, 21, 3490-3498.
Koh et al., "An Internal Ribosome Entry Site (IRES) Mutant Library for Tuning Expression Level of Multiple Genes in Mammalian Cells," PLOS One 2013, 8(12), e82100.
Kojima et al., "Toward a world of theranostic medication: Programming biological sentinel systems for therapeutic intervention," Advanced Drug Delivery Reviews 2016, 105, 66-76.
Lichty et al., "Vesicular stomatitis virus: re-inventing the bullet," Trends in Molecular Medicine 2004, 10(5), 210-216.
Lienert et al., "Synthetic biology in mammalian cells: Next generation research tools and therapeutics," Nature Reviews of Molecular Cell Biology 2014, 15(2), 95-107.
Lohmueller et al., "A tunable zinc finger-based framework for Boolean logic computation in mammalian cells," Nucleic Acids Research 2012, 40(11), 5180-5187.
Lonzaric et al., "Design and applications of synthetic information processing circuits in mammalian cells," Synthetic Biology 2018, 2, 1-34.
Ma et al., "Defining Network Topologies that Can Achieve Biochemical Adaptation," Cell 2009, 138, 760-773.

(56) References Cited

OTHER PUBLICATIONS

Marchisio et al., "Computational design of synthetic gene circuits with composable parts," Bioninformatics 2008, 24(17), 1903-1910.
Morsut et al., "Engineering Customized Cell Sensing and Response Behaviors Using Synthetic Notch Receptors," Cell 2016, 164(4), 780-791.
Nakanishi et al., Development of Sendai Virus Vectors and their Potential Applications in Gene Therapy and Regenerative Medicine, Current Gene Therapy 2012, 12, 410-416.
Nallamsetty et al., "Efficient site-specific processing of fusion proteins by tobacco vein mottling virus protease in vivo and in vitro," Protein Expression and Purification 2004, 38, 108-115.
Nelson, "Antibody fragments," mAbs 2010, 2(1), 77-83.
Nielsen et al., "Genetic circuit design automation," Science 2016, 352(6281), aac7341.
Nissim et al., "A tunable dual-promoter integrator for targeting of cancer cells," Molecular Systems Biology 2010, 6(444), 1-9.
Non-final Office Action dated Apr. 18, 2022 in U.S. Appl. No. 16/556,063.
Non-final Office Action dated Jun. 14, 2022 in U.S. Appl. No. 16/738,664.
Non-final Office Action dated Jun. 28, 2023 in U.S. Appl. No. 17/157,880.
Notice of Allowance dated Aug. 24, 2022 in U.S. Appl. No. 16/556,063.
Notice of Allowance dated Dec. 20, 2023 in U.S. Appl. No. 17/157,880.
Notice of Allowance dated Jan. 26, 2023 in U.S. Appl. No. 16/738,664.
Notice of Allowance dated May 18, 2022 in U.S. Appl. No. 16/555,604.
Notice of Allowance Dated Nov. 22, 2023 in U.S. Appl. No. 17/935,024.
Notice of Allowance Dated Sep. 16, 2020 in U.S. Appl. No. 16/250,314.
Oliveira et al., "An Improved Ras Sensor for Highly Sensitive and Quantitative FRET-FLIM Imaging," PLOS One 2013, 8(1), e52874.
Park et al., "Rewiring MAP Kinase Pathways Using Alternative Scaffold Assembly Mechanisms," Science 2003, 299, 1061-1064.
Partial European Search Report dated Nov. 19, 2021 in European Patent Application 19743690.0.
Porcher et al., "The Bicoid Morphogen System," Current Biology 2010, 20(5), R249-R254.
Pu et al., "Evolution of a split RNA polymerase as a versatile biosensor platform," Nature Chemical Biology 2017, 13(4), 432-438.
Reinke et al., "A synthetic coiled-coil interactome provides heterospecific modules for molecular engineering," Journal of the American Chemical Society 2010, 132(17), 6025-6031.
Restriction Requirement Dated Dec. 7, 2021 in U.S. Appl. No. 16/738,664.
Restriction Requirement Dated Dec. 9, 2019 in U.S. Appl. No. 16/250,314.
Restriction Requirement Dated Feb. 24, 2023 in U.S. Appl. No. 17/157,880.
Restriction Requirement Dated Sep. 28, 2021 in U.S. Appl. No. 16/556,063.
Riechmann et al., "Single domain antibodies: comparison of camel VH and camelised human VH domains," Journal of Immunological Methods 1999, 231, 25-38.
Rinaudo et al., "A universal RNAi-based logic evaluator that operates in mammalian cells," Nature Biotechnology 2007, 1-6.
Roquet et al., "Synthetic recombinase-based state machines in living cells," Science 2016, 353(6297), aad8559.
Rossi et al., "Monitoring protein-protein interactions in intact eukaryotic cells by b-galactosidase complementation," PNAS 1997, 94, 8405-8410.
Roybal et al., "Precision Tumor Recognition by T Cells With Combinatorial Antigen-Sensing Circuits," Cell 2016, 164, 770-779.
Russell et al., "Oncolytic Virotherapy," Nature Biotechnology 2012, 30(7).

Schnell et al., "Infectious rabies viruses from cloned cDNA," The EMBO Journal 1994, 13(18), 4195-4203.
Schwanhausser et al. "Global quantification of mammalian gene expression control" Nature 2011, 473, 337-342.
Shekhawat et al., "An Autoinhibited Coiled-Coil Design Strategy for Split-Protein Protease Sensors," J. Am. Chem Soc. 2009, 131, 15284-15290.
Snitkovsky et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," Journal of Virology 2000, 74(20), 9540-9545.
Stein et al., "Protease-based synthetic sensing and signal amplification," PNAS 2014, 1-6.
Stein et al., "Synthetic protein switches: design principles and applications," Trends in Biotechnology 2015, 33(2), 101-110.
Stein et al., "Ultrasensitive Scaffold-Dependent Protease Sensors with Large Dynamic Range," ACS Synthetic Biology 2017, 6, 1337-1342.
Stevens et al., "Design of a Split Intein with Exceptional Protein Splicing Activity," Journal of the American Chemical Society 2016, 138, 2162-2165.
Stricker et al. "A fast, robust and tunable synthetic gene oscillator," Nature 2008, 456, 516-520.
Supplementary Partial European Search Report dated Nov. 19, 2021 in European Application No. 19743690.0.
Szymczak et al., "Correction of multi-gene deficiency in vivo using a single 'self-cleaving' 2A peptide-based retroviral vector," Nature Biotechnology 2004, 22, 589-594.
Tang et al., "Detection and manipulation of live antigen-expressing cells using conditionally stable nanobodies," eLIFE 2016, 5, 1-27.
Taremi et al., "Construction, expression, and characterization of a novel fully activated recombinant single-chain hepatitis C virus protease," Protein Science 1998, 7, 2143-2149.
Taxis et al., "Efficient protein depletion by genetically controlled deprotection of a dormant N-degron," Molecular Systems Biology 2009, 5(267), 1-7.
To et al., "Rationally designed fluorogenic protease reporter visualizes spatiotemporal dynamics of apoptosis in vivo," PNAS 2015, 112(11), 3338-3343.
Tozser et al., "Comparison of the substrate specificity of two potyvirus proteases," The FEBS Journal 2005, 272, 514-523.
Truong et al., "Development of an intein-mediated split-Cas9 system for gene therapy," Nucleic Acids Research 2015, 43(13), 6450-6458.
Varshavsky, "The N-end rule: Functions, mysteries, uses," PNAS 1996, 93, 12142-12149.
Waugh, "An overview of enzymatic reagents for the removal of affinity tags," Protein Expression and Purification 2011.
Wehr et al., "Monitoring regulated protein-protein interactions using split TEV," Nature Methods 2006, 3(12), 985-993.
Weinberg et al., "Large-scale design of robust genetic circuits with multiple inputs and outputs for mammalian cells," Nature Biotechnology 2017, 35(5), 453-462.
Weinheimer et al., "Autoproteolysis of Herpes Simplex Virus Type 1 Protease Releases an Active Catalytic Domain Found in Intermediate Capsid Particles," Journal of Virology 1993, 67(10), 5813-5822.
Wikstrand et al., "The class III variant of the epidermal growth factor receptor (EGFRvIII): characterization and utilization as an immunotherapeutic target," Journal of NeuroVirology 1998, 4, 148-158.
Wroblewska et al., "Mammalian synthetic circuits with RNA binding proteins delivered by RNA," Nature Biotechnology 2015, 33(8), 839-841.
Wu, Yiqian, and Yingxiao Wang. "Protein circuits reprogram cells." Nature chemical biology 15.2 (2019): 96-97.
Xie et al., "Multi-Input RNAi-Based Logic Circuit for Identification of Specific Cancer Cells," Science 2011, 333, 1307-1311.
Yasuda et al., "Supersensitive Ras activation in dendrites and spines revealed by two-photon fluorescence lifetime imaging," Nature Neuroscience 2006, 9(2), 283-291.

(56) References Cited

OTHER PUBLICATIONS

Yeh et al., "Rewiring cellular morphology pathways with synthetic guanine nucleotide exchange factors," Nature 2007, 447, 596-600.
Zetche et al., "A Split Cas9 Architecture for Inducible Genome Editing and Transcription Modulation," Nature Biotechnology 2015, 33(2), 139-142.

* cited by examiner

SEQUENCE LISTING

```
Sequence total quantity: 11
SEQ ID NO: 1            moltype = AA  length = 231
FEATURE                 Location/Qualifiers
REGION                  1..231
                        note = nTVMVP-CfaN
REGION                  4..121
                        note = nTVMVPmut
REGION                  127..230
                        note = CfaN
source                  1..231
```

```
                          mol_type = protein
                          organism = synthetic construct
SEQUENCE: 1
MGSSKALLKG VRDFNPISAC VCLLENSSDG HSERLFGIGF GPYIIANQRL FRRNNGELTI    60
KTMHGEFKVK NSTQLQMKPV EGRNIIVIKM AKDFPPFPQK LKFRQPTIKD RVCMVSTNFQ   120
QGSGSSAEYC LSYDTEILTV EYGFLPIGKI VEERIECTVY TVDKNGFVYT QPIAQWHNRG   180
EQEVFEYCLE DGSIIRATKD HKFMTTDGQM LPIDEIFERG LDLKQVDGLP S            231

SEQ ID NO: 2              moltype = AA   length = 164
FEATURE                   Location/Qualifiers
REGION                    1..164
                          note = CfaC-cTVMVP
REGION                    4..41
                          note = CfaC
REGION                    47..163
                          note = cTVMVP
source                    1..164
                          mol_type = protein
                          organism = synthetic construct
SEQUENCE: 2
MGSVKIISRK SLGTQNVYDI GVEKDHNFLL KNGLVASNCF NGGSGKSVS SLVSESSHIV    60
HKEDTSFWQH WITTKDGQCG SPLVSIIDGN ILGIHSLTHT TNGSNYFVEF PEKFVATYLD   120
AADGWCKNWK FNADKISWGS FTLVEDAPED DFMAKKTVAA IMDS                    164

SEQ ID NO: 3              moltype = AA   length = 178
FEATURE                   Location/Qualifiers
REGION                    1..178
                          note = nTVMVP-CfaN2
REGION                    4..121
                          note = nTVMVP
REGION                    127..177
                          note = CfaN2
source                    1..178
                          mol_type = protein
                          organism = synthetic construct
SEQUENCE: 3
MGSSKALLKG VRDFNPISAC VCLLENSSDG HSERLFGIGF GPYIIANQHL FRRNNGELTI    60
KTMHGEFKVK NSTQLQMKPV EGRDIIVIKM AKDFPPFPQK LKFRQPTIKD RVCMVSTNFQ   120
QGSGSSGEQE VFEYCLEDGS IIRATKDHKF MTTDGQMLPI DEIFERGLDL KQVDGLPS     178

SEQ ID NO: 4              moltype = AA   length = 273
FEATURE                   Location/Qualifiers
REGION                    1..273
                          note = CZp-nTVMVPmut-tevsCfaN
REGION                    4..33
                          note = CZp
REGION                    44..161
                          note = nTVMVPmut
REGION                    167..272
                          note = TEV-cleavable CfaN
REGION                    204..210
                          note = TEV cleavage site
source                    1..273
                          mol_type = protein
                          organism = synthetic construct
SEQUENCE: 4
MGSEQLEKKL QALEKKLAQL EWKNQALEKK LAQGGSGSGS GSSSKALLKG VRDFNPISAC    60
VCLLENSSDG HSERLFGIGF GPYIIANQRL FRRNNGELTI KTMHGEFKVK NSTQLQMKPV   120
EGRNIIVIKM AKDFPPFPQK LKFRQPTIKD RVCMVSTNFQ QGSGSSAEYC LSYDTEILTV   180
EYGFLPIGKI VEERIECTVY TVDENLYFQS YTQPIAQWHN RGEQEVFEYC LEDGSIIRAT   240
KDHKFMTTDG QMLPIDEIFE RGLDLKQVDG LPS                                273

SEQ ID NO: 5              moltype = AA   length = 276
FEATURE                   Location/Qualifiers
REGION                    1..276
                          note = CZp-nTVMVPmut-tevsCfaN
REGION                    4..33
                          note = CZp
REGION                    45..161
                          note = nTVMVPmut
REGION                    167..275
                          note = TEV-cleavable CfaN
REGION                    174..180
                          note = TEV cleavage site
source                    1..276
                          mol_type = protein
                          organism = synthetic construct
SEQUENCE: 5
MGSEQLEKKL QALEKKLAQL EWKNQALEKK LAQGGSGSGS GSSSKALLKG VRDFNPISAC    60
```

```
VCLLENSSDG HSERLFGIGF GPYIIANQRL FRRNNGELTI KTMHGEFKVK NSTQLQMKPV    120
EGRNIIVIKM AKDFPPFPQK LKFRQPTIKD RVCMVSTNFQ QGSGSSAEYC LSYENLYFQS    180
EILTVEYGFL PIGKIVEERI ECTVYTVDKN GFVYTQPIAQ WHNRGEQEVF EYCLEDGSII    240
RATKDHKFMT TDGQMLPIDE IFERGLDLKQ VDGLPS                              276

SEQ ID NO: 6           moltype = AA  length = 272
FEATURE                Location/Qualifiers
REGION                 1..272
                       note = TEVP-NZp
REGION                 4..239
                       note = TEVP
REGION                 243..271
                       note = NZp
source                 1..272
                       mol_type = protein
                       organism = synthetic construct
SEQUENCE: 6
MGSGESLFKG PRDYNPISST ICHLTNESDG HTTSLYGIGF GPFIITNKHL FRRNNGTLLV    60
QSLHGVFKVK NTTTLQQHLI DGRDMIIIRM PKDFPPFPQK LKFREPQREE RICLVTTNFQ   120
TKSMSSMVSD TSCTFPSSDG IFWKHWIQTK DGQCGSPLVS TRDGFIVGIH SASNFTNTNN   180
YFTSVPKNFM ELLTNQEAQQ WVSGWRLNAD SVLWGGHKVF MVKPEEPFQP VKEATQLMNS   240
GGALKKELQA NKKELAQLKW ELQALKKELA QS                                 272

SEQ ID NO: 7           moltype = AA  length = 104
FEATURE                Location/Qualifiers
REGION                 1..104
                       note = CfaN
source                 1..104
                       mol_type = protein
                       organism = synthetic construct
SEQUENCE: 7
AEYCLSYDTE ILTVEYGFLP IGKIVEERIE CTVYTVDKNG FVYTQPIAQW HNRGEQEVFE    60
YCLEDGSIIR ATKDHKFMTT DGQMLPIDEI FERGLDLKQV DGLP                    104

SEQ ID NO: 8           moltype = AA  length = 38
FEATURE                Location/Qualifiers
REGION                 1..38
                       note = CfaC
source                 1..38
                       mol_type = protein
                       organism = synthetic construct
SEQUENCE: 8
VKIISRKSLG TQNVYDIGVE KDHNFLLKNG LVASNCFN                            38

SEQ ID NO: 9           moltype = AA  length = 51
FEATURE                Location/Qualifiers
REGION                 1..51
                       note = CfaN2
source                 1..51
                       mol_type = protein
                       organism = synthetic construct
SEQUENCE: 9
GEQEVFEYCL EDGSIIRATK DHKFMTTDGQ MLPIDEIFER GLDLKQVDGL P              51

SEQ ID NO: 10          moltype = AA  length = 106
FEATURE                Location/Qualifiers
REGION                 1..106
                       note = TEV-cleavable CfaN
REGION                 38..44
                       note = TEV cleavage site
source                 1..106
                       mol_type = protein
                       organism = synthetic construct
SEQUENCE: 10
AEYCLSYDTE ILTVEYGFLP IGKIVEERIE CTVYTVDENL YFQSYTQPIA QWHNRGEQEV    60
FEYCLEDGSI IRATKDHKFM TTDGQMLPID EIFERGLDLK QVDGLP                  106

SEQ ID NO: 11          moltype = AA  length = 109
FEATURE                Location/Qualifiers
REGION                 1..109
                       note = TEV-cleavable CfaN
REGION                 8..14
                       note = TEV cleavage site
source                 1..109
                       mol_type = protein
                       organism = synthetic construct
```

```
-continued

SEQUENCE: 11
AEYCLSYENL YFQSEILTVE YGFLPIGKIV EERIECTVYT VDKNGFVYTQ PIAQWHNRGE    60
QEVFEYCLED GSIIRATKDH KFMTTDGQML PIDEIFERGL DLKQVDGLP              109
```

SYNTHETIC SYSTEM FOR TUNABLE THRESHOLDING OF PROTEIN SIGNALS

RELATED APPLICATIONS

This application is a continuation of U.S. application Ser. No. 16/738,664, filed Jan. 10, 2020, which claims the benefit under 35 U.S.C. § 119(e) of U.S. Provisional Patent Application Ser. No. 62/790,553, filed Jan. 10, 2019, the content of this related application is incorporated herein by reference in its entirety for all purposes.

STATEMENT REGARDING FEDERALLY SPONSORED R&D

This invention was made with government support under Grant No. GM007616 awarded by the National Institutes of Health and Grant No. HR0011-17-2-0008 awarded by DARPA. The government has certain rights in the invention.

REFERENCE TO SEQUENCE LISTING

The present application is being filed along with a Sequence Listing in electronic format. The Sequence Listing is provided as a file entitled 30KJ-302415-US_Sequence-Listing, created May 10, 2023, which is 23 kilobytes in size. The information in the electronic format of the Sequence Listing is incorporated herein by reference in its entirety.

BACKGROUND

Field

The present disclosure relates generally to the field of synthetic biology.

Description of the Related Art

Synthetic biology may enable design of new functions in living cells. Many natural cellular functions are implemented by protein-level circuits, in which proteins specifically modify each other's activity, localization, or stability. Synthetic protein circuits could provide advantages over gene regulation circuits in enabling the design of new functions in living cells. There is a need for synthetic protein circuits that respond to inputs only above (or below) a certain threshold concentration.

SUMMARY

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first partner domain is capable of binding the second partner domain, wherein the first polypeptide domain and the second polypeptide domain are capable of associating with each other to constitute a first protein capable of being in a first protein active state when the first partner domain binds the second partner domain; and a thresholding polypeptide comprising a third partner domain and a third polypeptide domain, wherein the third partner domain is capable of binding the second partner domain, wherein the first protein is not in the first protein active state when the third partner domain binds the second partner domain.

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the first input polypeptide and the third input polypeptide are in close proximity.

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the second input polypeptide and the third input polypeptide are in close proximity.

In some embodiments, the first protein in the first protein active state is capable of generating a thresholding output. In some embodiments, the thresholding output comprises a first enzymatic reaction with a substrate generating a first product. In some embodiments, the third polypeptide domain and the second polypeptide domain are incapable of associating to form the first protein in the first protein active state. In some embodiments, the first polypeptide domain and the second polypeptide domain have weak association affinity.

In some embodiments, the third polypeptide domain comprises less than 50% homology to the first polypeptide domain. In some embodiments, the third polypeptide domain is a variant of the first polypeptide domain. In some embodiments, the third polypeptide domain and the second polypeptide domain are capable of associating with each other to constitute a first protein capable of being in a first protein inactive state when the third partner domain binds the second partner domain. In some embodiments, the third polypeptide domain and the second polypeptide domain are capable of associating with each other to constitute a first protein capable of being in a first protein dominant negative state when the third partner domain binds the second partner domain. In some embodiments, the first protein in a first protein dominant negative state is capable of reducing or preventing the first enzymatic reaction.

In some embodiments, the first protein in a first protein active state comprises hydrolase activity, transferase activity, lyase activity, isomerase activity, ligase activity, oxidoreductase activity, or any combination thereof. In some embodiments, the first protein in a first protein active state comprises fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. In some embodiments, the first protein in a first protein active state comprises nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof. In some embodiments, the substrate comprises a nucleic acid, a protein, a lipid, or any combination thereof. In some embodiments, the first protein comprises a thresholding output protease. In some embodiments, the first protein comprises a polymerase, wherein the polymerase comprises T7 RNA polymerase, T3 RNA polymerase, SP6 RNA polymerase, RNA polymerase I, RNA polymerase II, RNA polymerase III, RNA polymerase IV, or RNA polymerase V, T7 DNA polymerase, eukaryotic mitochondrial DNA Polymerase γ, prokaryotic DNA polymerase I, prokaryotic DNA polymerase II, prokaryotic DNA polymerase III, prokaryotic DNA polymerase IV, prokaryotic DNA polymerase V, eukaryotic polymerase α, eukaryotic polymerase β, eukaryotic polymerase γ, eukaryotic polymerase δ, eukaryotic polymerase ε, eukaryotic polymerase η, eukaryotic polymerase ζ, eukaryotic polymerase ι, eukaryotic polymerase κ, *E. coli* DNA polymerase I, *E. coli* DNA polymerase III alpha subunit, *E. coli* DNA polymerase III epsilon subunits, *E. coli* polymerase IV, *E. coli* polymerase V, *T. aquaticus* DNA polymerase I, *B. stearothermophilus* DNA polymerase I, a *Euryarchaeota* polymerase, terminal deoxynucleotidyl transferase (TdT), *S. cerevisiae* polymerase 4, a translesion synthesis polymerase, reverse transcriptase, a thermostable polymerase, a telomerase, or any combination thereof.

In some embodiments, the first protein comprises an RNA-binding domain, a DNA-binding domain, a transactivation domain, a nuclear receptor ligand binding domain, or any combination thereof. In some embodiments, the DNA-binding domain and/or RNA-biding domain comprise dCas9, Gal4, hypoxia inducible factor (HIF), HIF 1a, cyclic AMP response element binding (CREB) protein, LexA, rtTA, an endonuclease, a zinc finger binding domain, a transcription factor, portions thereof, or any combination thereof. In some embodiments, the transactivation domain comprises VP16, TA2, VP64 (a tetrameric repeat of the minimal activation domain of VP16), signal transducer and activator of transcription 6 (STAT6), reticuloendotheliosis virus A oncogene (relA), TATA binding protein associated factor-1 (TAF-1), TATA binding protein associated factor-2 (TAF-2), glucocorticoid receptor TAU-1, or glucocorticoid receptor TAU-2, a steroid/thyroid hormone nuclear receptor transactivation domain, a polyglutamine transactivation domain, a basic or acidic amino acid transactivation domain, a GAL4 transactivation domain, an NF-κB transactivation domain, a p65 transactivation domain, a BP42 transactivation domain, portions thereof having transcription activating activity, or any combination thereof. In some embodiments, the first protein comprises Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, and any combination thereof. In some embodiments, the first protein comprises Cas9, Cpf1, Cas13a, or a variant or derivative thereof.

In some embodiments, the synthetic protein circuit further comprise a tuner polypeptide, wherein the tuner polypeptide is capable of modulating the concentration, localization, stability, and/or activity of the thresholding polypeptide. In some embodiments, the tuner polypeptide is capable of diminishing the concentration, stability, and/or activity of the thresholding polypeptide. In some embodiments, the tuner polypeptide comprises a first thresholding protease, wherein the first thresholding protease in a first thresholding protease active state is capable of cutting a first thresholding protease cut site of the thresholding polypeptide. In some embodiments, the third partner domain comprises the first thresholding protease cut site. In some embodiments, the thresholding polypeptide comprises a degron, wherein the first thresholding protease in the first thresholding protease active state is capable of cutting the first thresholding protease cut site of the thresholding polypeptide to expose the degron, and wherein the degron of the thresholding polypeptide being exposed changes the thresholding polypeptide to a thresholding polypeptide destabilized state.

In some embodiments, the first partner domain, second partner domain, and/or third partner domain comprise an intein-N, an intein-C, a fragment thereof, or any combination thereof. In some embodiments, the first partner domain, second partner domain, and/or third partner domain comprise CfaN, CfaC, NpuC, NpuN, gp41-1, gp41-2, gp41-3, gp41-4, gp41-5, gp41-6, gp41-7, gp41-8, IMPDH-1, NrdA-1, NrdA-2, NrdA-4, NrdA-5, NrdA-6, NrdJ-1, NrdJ-2 a fragment thereof, or any combination thereof. In some embodiments, the first partner domain comprises an amino acid sequence at least 50, 60, 70, 75, 80, 85, 90, 95, 96, 97, 98, or 99 percent identical to SEQ ID NO: 9. In some embodiments, the second partner domain comprises an amino acid sequence at least 50, 60, 70, 75, 80, 85, 90, 95, 96, 97, 98, or 99 percent identical to SEQ ID NO: 8. In some embodiments, the third partner domain comprises an amino acid sequence at least 50, 60, 70, 75, 80, 85, 90, 95, 96, 97, 98, or 99 percent identical to any one of SEQ ID NOs: 7, 10, and 11.

In some embodiments, the third partner domain and the second partner domain are capable of inducing trans-splicing of the thresholding polypeptide and second input polypeptide when the second partner domain binds the third partner domain, thereby generating a conjugate comprising the second polypeptide domain and the third polypeptide domain. In some embodiments, the conjugate is not capable of being in the first protein active state. In some embodiments, the conjugate is not capable of catalyzing the first enzymatic reaction. In some embodiments, the second polypeptide comprises a first half of an elimination site adjacent to the second partner domain, wherein the thresholding polypeptide comprises a second half of the elimination site adjacent to the third partner domain, and wherein the conjugate comprises an intact elimination site. In some embodiments, the intact elimination site is capable of inducing the sequestering of the conjugate. In some embodiments, the elimination site comprises a nuclear localization signal (NLS) or a nuclear export signal (NES). In some embodiments, the intact elimination site is capable of destabilizing the conjugate. In some embodiments, the elimination site comprises a second thresholding protease cut site a second thresholding protease in a second thresholding protease active state is capable of cutting. In some embodiments, the second input polypeptide and/or thresholding polypeptide comprise a degron, wherein the conjugate comprises a degron adjacent to the second thresholding protease cut site, wherein the second thresholding protease in the second thresholding protease active state is capable of cutting the second thresholding protease cut site of the conjugate to expose the degron, and wherein the degron of the conjugate being exposed changes the conjugate to a conjugate destabilized state.

In some embodiments, the first partner domain is configured to have a reduced binding affinity for the second partner domain as compared to the binding affinity of the third partner domain for the second partner domain. In some embodiments, first partner domain and second partner domain are homodimers. In some embodiments, first partner domain and second partner domain are heterodimers. In some embodiments, the third partner domain comprises at most 99% homology to the first partner domain. In some embodiments, the third partner domain comprises at least 70% homology to the first partner domain. In some embodiments, the binding between the first partner domain and the second partner domain is reversible. In some embodiments, the binding between the third partner domain and the second partner domain is reversible. In some embodiments, the binding between the third partner domain and the second partner domain is irreversible.

In some embodiments, the first partner domain binds the second partner domain with a first binding affinity, and wherein the third partner domain binds the second partner domain with a second binding affinity. In some embodiments, the second binding affinity is equivalent to the first binding affinity. In some embodiments, the second binding affinity is at least 10 percent greater than the first binding affinity, or the first binding affinity is at least 10 percent greater than the second binding affinity. In some embodiments, the first partner domain is a variant of the third partner domain that are configured to reduce the first binding affinity, wherein the first partner domain comprises one or more mutations as compared to the third partner domain. In some embodiments, the one or more mutations reduce the first binding affinity by at least 10 percent as compared to the second binding affinity.

In some embodiments, the first partner domain, second partner domain, and/or third partner domain comprise SYNZIP1, SYNZIP2, SYNZIP3, SYNZIP4, SYNZIP5, SYNZIP6, SYNZIP7, SYNZIP8, SYNZIP9, SYNZIP10, SYNZIP11, SYNZIP12, SYNZIP13, SYNZIP14, SYNZIP15, SYNZIP16, SYNZIP17, SYNZIP18, SYNZIP19, SYNZIP20, SYNZIP21, SYNZIP22, SYNZIP23, BATF, FOS, ATF4, BACH1, JUND, NFE2L3, AZip, BZip, or any combination thereof. In some embodiments, the first partner domain, second partner domain, and/or third partner domain comprise a PDZ domain and/or a PDZ domain ligand. In some embodiments, the first partner domain, second partner domain, and/or third partner domain comprise an SH3 domain, a PDZ domain, a GTPase binding domain, a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, a bZIP domain, portions thereof, variants thereof, or any combination thereof.

In some embodiments, the first partner domain, second partner domain, and/or third partner domain comprise a signal transducer binding domain. In some embodiments, the first partner domain, second partner domain, and/or third partner domain comprise a signal transducer binding domain capable of binding to a signal transducer in a signal transducer active state. In some embodiments, the first partner domain, second partner domain, and/or third partner domain comprise a signal transducer binding domain capable of binding to a signal transducer in a signal transducer inactive state. In some embodiments, the first partner domain, second partner domain, and/or third partner domain comprise a RAS binding domain (RBD) and/or RAS association domain (RAD). In some embodiments, the first partner domain and second partner domain are a pair of constitutive protein partner domains selected from the group consisting of (a) cognate leucine zipper domains, (b) cognate PSD95-Dlgl-Zo-1 (PDZ) domains, (c) a streptavidin domain and cognate streptavidin binding protein (SBP) domain, (d) a PYL domain and cognate ABI domain, (e) a pair of cognate zinc finger domains, (f) a pair of cognate SH3 domains, and (g) a peptide and antibody or antigen-binding fragment thereof that specifically binds to the peptide. In some embodiments, the first partner domain, second partner domain, and/or third partner domain comprise CZp, NZp, or any combination thereof.

In some embodiments, a thresholding output level is related to a number of molecules of the first protein in a first protein active state. In some embodiments, a thresholding output level is related to a number of molecules of the first product. In some embodiments, the thresholding output is generated in response to a first input. In some embodiments, a first output is generated in response to the first input, wherein a first output level correlates (e.g., positively correlates) with a first input level. In some embodiments, the thresholding output is generated in response to the first output. In some embodiments, the first output modulates the localization of second input polypeptide, the generation of the second input polypeptide, the stability of the second input polypeptide, and/or the second input polypeptide concentration. In some embodiments, the generation of the second input polypeptide, the stability of the second input polypeptide, the activity of the second input polypeptide, and/or the second input polypeptide concentration correlates (e.g., positively correlates) with the first output level and/or the first input level. In some embodiments, a precursor second input polypeptide comprises a first cut site, wherein the first polypeptide domain and the second polypeptide domain are incapable of associating with each other to constitute a first protein capable of being in a first protein active state when the first cut site is intact. In some embodiments, the first output comprises a first protease in a first protease active state. In some embodiments, the first output level is related to a number of molecules of the first protease in a first protease active state. In some embodiments, the first output comprises the first protease in the first protease active state cutting the first cut site of the precursor second input polypeptide, thereby generating the second input polypeptide.

In some embodiments, no thresholding output is generated below a threshold first input level. In some embodiments, the thresholding output level generated below a threshold first input level is less than about 5% as compared to the thresholding output level generated at or above the threshold first input level. In some embodiments, the threshold first input level in the absence of the thresholding input polypeptide is a basal threshold first input level. In some embodiments, the threshold first input level in the presence of a first thresholding polypeptide concentration and in the presence of a first tuner polypeptide concentration is a first threshold first input level. In some embodiments, the threshold first input level in the presence of a first thresholding polypeptide concentration and in the presence of a second tuner polypeptide concentration is a second threshold first input level. In some embodiments, the threshold first input level in the presence of a second thresholding polypeptide concentration and in the presence of a first tuner polypeptide concentration is a third threshold first input level. In some embodiments, the first threshold first input level, the second threshold first input level, and/or the third threshold first input level is at least about 2-fold higher than the basal threshold first input level. In some embodiments, no thresholding output is generated below a threshold second input polypeptide concentration. In some embodiments, the thresholding output level generated below a threshold second input polypeptide concentration is less than about 5% as compared to the thresholding output level generated at or above the threshold second input polypeptide concentration. In some embodiments, the threshold second input polypeptide concentration in the absence of the thresholding input polypeptide is a basal threshold second input polypeptide concentration. In some embodiments, the threshold second input polypeptide concentration in the presence of a first thresholding polypeptide concentration and in the presence of a first tuner polypeptide concentration is a first threshold second input polypeptide concentration. In some embodiments, the threshold second input polypeptide concentration in the presence of a first thresholding polypeptide concentration and in the presence of a second tuner polypeptide concentration is a second threshold second input polypeptide concentration. In some embodiments, the threshold second input polypeptide concentration in the presence of a second thresholding polypeptide concentration and in the presence of a first tuner polypeptide concentration is a third threshold second input polypeptide concentration. In some embodiments, the first threshold second input polypeptide concentration, the second threshold second input polypeptide concentration, and/or the third threshold second input polypeptide concentration is at least about 2-fold higher than the basal threshold second input polypeptide concentration. In some embodiments, the second tuner polypeptide concentration is at least 1.1-fold higher than the first tuner polypeptide concentration. In some embodiments, the second thresholding polypeptide concentration is at least 1.1-fold higher than the first thresholding polypeptide concentration.

In some embodiments, the first input level correlates (e.g., positively correlates) with a first level of activation of a first signal transducer and/or a second level of activation of a second signal transducer. In some embodiments, the first output level correlates (e.g., positively correlates) with a first level of activation of a first signal transducer and/or a second level of activation of the second signal transducer. In some embodiments, the first level of activation of the first signal transducer is related to a number of molecules of the first signal transducer in a first transducer active state, and/or wherein the second level of activation of the second signal transducer is related to a number of molecules of the second signal transducer in a second transducer active state In some embodiments, the synthetic protein circuit is capable of directly or indirectly inducing cell death in the presence of the aberrant signaling of a first signal transducer, or when a first level of activation of the first signal transducer is above a first signal transducer activation threshold. In some embodiments, the substrate comprises Caspase-3, Caspase 7, Caspase-9, Caspase-8, Bax, Bid, Bad, Bak, BCL2L11, p53, PUMA, Diablo/SMAC, S-TRAIL, or any combination thereof. In some embodiments, the first signal transducer, the second signal transducer, or both comprise AKT, PI3K, MAPK, p44/42 MAP kinase, TYK2, p38 MAP kinase, PKC, PKA, SAPK, ELK, INK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCγ, NF-kB, FAK, CREB, αIIIβ3, FcεRI, BAD, p70S6K, STAT1, STAT2, STAT3, STAT5, STAT6, or any combination thereof.

Disclosed herein include methods of thresholding protein signals. In some embodiments, the method comprises expressing a synthetic protein circuit disclosed herein in a cell. Disclosed herein include methods of modulating the threshold concentration of an input species needed to generate a output protein species. In some embodiments, the method comprises expressing a synthetic protein circuit disclosed herein in a cell. Disclosed herein include methods of modulating a threshold first input level. In some embodiments, the method comprises expressing a synthetic protein circuit disclosed herein in a cell. Disclosed herein include methods of modulating a threshold second input polypeptide concentration. In some embodiments, the method comprises expressing a synthetic protein circuit disclosed herein in a cell. Disclosed herein include methods of treating a disease or disorder. In some embodiments, the method comprises expressing a synthetic protein circuit disclosed herein in a cell of a subject in need thereof. Disclosed herein include nucleic acids. In some embodiments, the nucleic acid encodes one or more components of a synthetic protein circuit disclosed herein.

In some embodiments, the disease or disorder is characterized by an aberrant signaling of one or more signal transducers. In some embodiments, the disease or disorder is characterized by an aberrant signaling of a RAS protein, the disease or disorder is a cancer, the disease or disorder is a RASopathy selected from the group comprising Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, Legius syndrome, or any combination thereof, the disease is a neurological disease or a neurodegenerative disease, the disease is an autoimmune disease, or the disease is infectious disease. In some embodiments the method comprises administering a prodrug, optionally wherein the prodrug is 5-fluorocytosine (5-FC) or ganciclovir. In some embodiments, the expressing comprises administering a nucleic acid encoding the synthetic protein circuit. In some embodiments, the expressing comprises administering two or more nucleic acids, and wherein the two or more nucleic acids encode the synthetic protein circuit. In some embodiments, the nucleic acid comprises at least one regulatory element for expression of the synthetic protein circuit. In some embodiments, the nucleic acid comprises a vector. In some embodiments, the vector comprises a adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector comprises an RNA viral vector. In some embodiments, the vector is derived from one or more negative-strand RNA viruses of the order Mononegavirales. In some embodiments, the vector is a rabies viral vector. In some embodiments, the administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof.

BRIEF DESCRIPTION OF THE DRAWINGS

FIGS. 3A-3B depict the design of a CHOMP thresholding module. FIG. 3A depicts a legend for the symbols shown in FIGS. 3C and 3F. FIGS. 3D-3E depict data related to operation of a CHOMP thresholding module in HEK293T cells comprising components shown in FIG. 3C. FIG. 3G depicts data related to operation of a CHOMP thresholding module regulatable by TEV protease tuner comprising components shown in FIG. 3F.

DETAILED DESCRIPTION

Figure 1A:
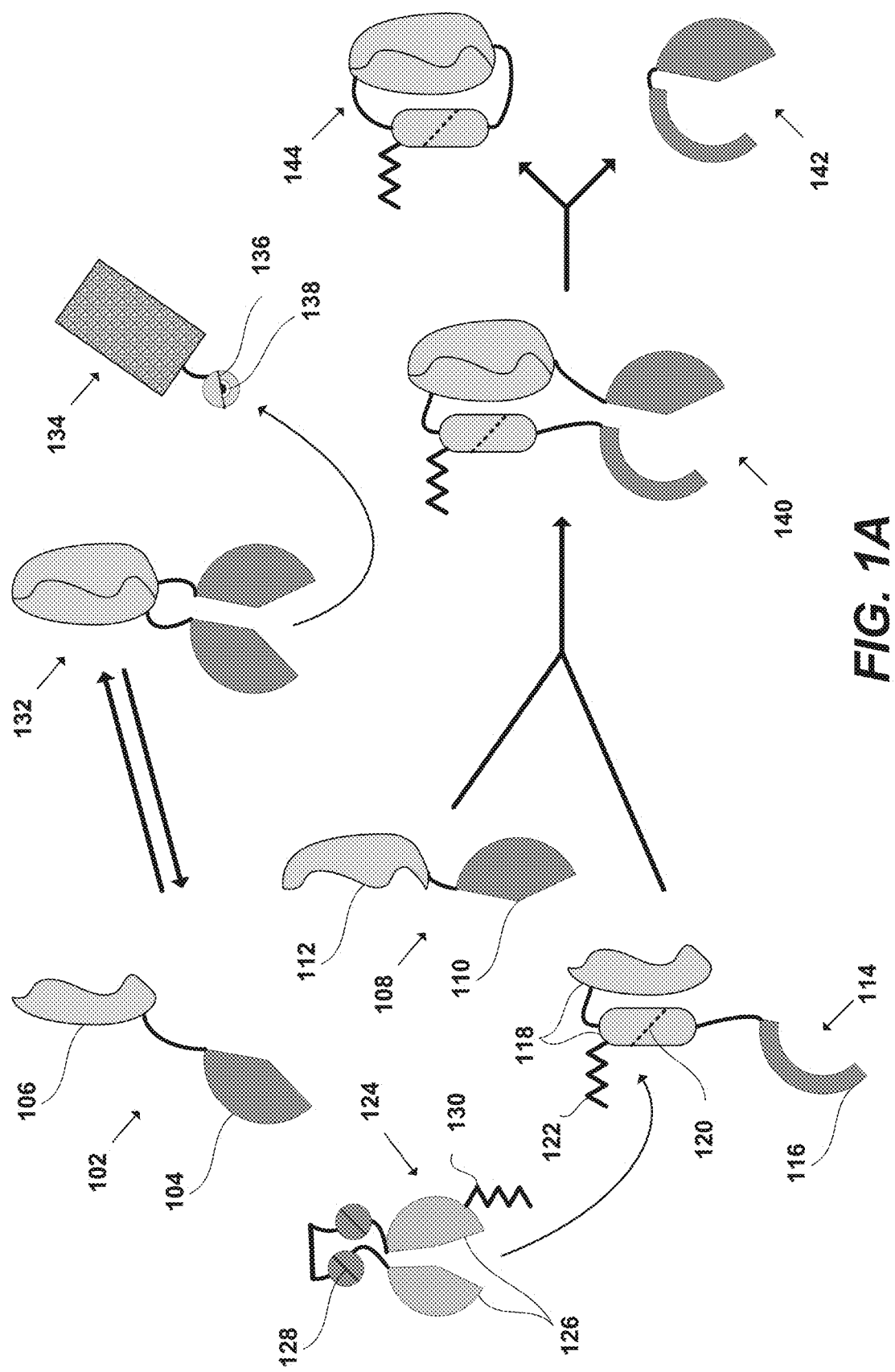
FIGS. 1A-1D show non-limiting exemplary schematic illustrations of synthetic protein circuits provided herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first partner domain is capable of binding the second partner domain, wherein the first polypeptide domain and the second polypeptide domain are capable of associating with each other to constitute a first protein capable of being in a first protein active state when the first partner domain binds the second partner domain; and a thresholding polypeptide comprising a third partner domain and a third polypeptide domain, wherein the third partner domain is capable of binding the second partner domain, wherein the first protein is not in the first protein active state when the third partner domain binds the second partner domain.

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the first input polypeptide and the third input polypeptide are in close proximity.

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the second input polypeptide and the third input polypeptide are in close proximity.

Disclosed herein include methods of thresholding protein signals. In some embodiments, the method comprises expressing a synthetic protein circuit disclosed herein in a cell. Disclosed herein include methods of modulating the threshold concentration of an input species needed to generate a output protein species. In some embodiments, the method comprises expressing a synthetic protein circuit disclosed herein in a cell. Disclosed herein include methods of modulating a threshold first input level. In some embodiments, the method comprises expressing a synthetic protein circuit disclosed herein in a cell. Disclosed herein include methods of modulating a threshold second input polypeptide concentration. In some embodiments, the method comprises expressing a synthetic protein circuit disclosed herein in a cell. Disclosed herein include methods of treating a disease or disorder. In some embodiments, the method comprises expressing a synthetic protein circuit disclosed herein in a cell of a subject in need thereof. Disclosed herein include nucleic acids. In some embodiments, the nucleic acid encodes one or more components of a synthetic protein circuit disclosed herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, N Y 1989). For purposes of the present disclosure, the following terms are defined below.

As used herein, the term "vector" refers to a polynucleotide construct, typically a plasmid or a virus, used to transmit genetic material to a host cell (e.g., a target cell). Vectors can be, for example, viruses, plasmids, cosmids, or phage. A vector can be a viral vector. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The terms "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, 2A sequences or elements refer to small peptides introduced as a linker between two proteins, allowing autonomous intraribosomal self-processing of polyproteins (See e.g., de Felipe. Genetic Vaccines and Ther. 2: 13 (2004); de Felipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The terms "treat" and "treatment" include, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may reduce the level of RAS signaling in the subject, thereby to reduce, alleviate, or eradicate the symptom(s) of the disease(s). As used herein, the term "prevention" refers to any activity that reduces the burden of the individual later expressing those RAS-related disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, ammo acids, carbohydrates including glucose, mannose, or dextrins, chelating agents such as EDTA, sugar alcohols such as mannitol or sorbitol, salt-forming counterions such as sodium, and nonionic surfactants such as Tween, polyethylene glycol (PEG), and Pluronics. Auxiliary, stabilizer, emulsifier, lubricant, binder, pH adjuster controller, isotonic agent and other conventional additives may also be added to the carriers.

Thresholding Synthetic Protein Circuits

Synthetic biology involves programming new functions in living cells. These include potential therapeutic systems that can be introduced into cells to recognize disease states and activate therapeutic responses. Synthetic biology allows for rational design of circuits that confer new functions in living cells. Many natural cellular functions are implemented by protein-level circuits, in which proteins specifically modify each other's activity, localization, or stability. Synthetic protein circuits have been described in, Gao, Xiaojing J., et al. "Programmable protein circuits in living cells." Science 361.6408 (2018): 1252-1258; U.S. application Ser. No. 16/556,063, filed on Aug. 29, 2019; and PCT Application published as WO 2019/147478; the content of each of these, including any supporting or supplemental information or material, is incorporated herein by reference in its entirety. The thresholding synthetic protein circuits provided herein can situated into a larger synthetic protein circuit comprising one or more synthetic protein circuit design components and/or concepts of Gao, Xiaojing J., et al., U.S. application Ser. No. 16/556,063, and/or WO 2019/147478. In some embodiments, the thresholding synthetic protein circuits provided herein can comprise one or more synthetic protein circuit design components and/or concepts of Gao, Xiaojing J., et al., U.S. application Ser. No. 16/556,063, and/or WO 2019/147478.

For many biological functions, it is important to be able to engineer circuits that respond to inputs only above (or below) a certain threshold concentration. An ideal thresholding module should enable tunable control of the threshold value itself, and ideally should also provide ultrasensitive responses (Ferrell et al, Trends Biochem Sci 2014). The synthetic protein circuits and methods provided herein address the above-mentioned needs. In some embodiments, the thresholding module provided herein be further regulated by an additional protein-level input (e.g., a tuner polypeptide as provided herein) tune or modulate the effects of the thresholding module (e.g., adjusts the threshold level). The new thresholding circuit design concept provided herein enables tunable control of the threshold value for a variety of different protein outputs in the context a number of different circuit types. Moreover, the synthetic protein circuits provided herein can be configured in numerous ways to generate regulatory cascades, binary logic gates, and dynamic analog signal-processing functions. The flexibility and scalability of this system enables it to be reconfigured to implement a broad range of additional functions.

Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first partner domain is capable of binding the second partner domain, wherein the first polypeptide domain and the second polypeptide domain are capable of associating with each other to constitute a first protein capable of being in a first protein active state when the first partner domain binds the second partner domain; and a thresholding polypeptide comprising a third partner domain and a third polypeptide domain, wherein the third partner domain is capable of binding the second partner domain, wherein the first protein is not in the first protein active state when the third partner domain binds the second partner domain. In some embodiments, the first protein in the first protein active state is capable of generating a thresholding output. In some embodiments, the thresholding output comprises a first enzymatic reaction with a substrate generating a first product. In some embodiments, the third polypeptide domain and the second polypeptide domain are incapable of associating to form the first protein in the first protein active state. In some embodiments, the first polypeptide domain and the second polypeptide domain have weak association affinity.

Some embodiments of the synthetic protein circuits provided herein further comprise a tuner polypeptide. The tuner polypeptide can be capable of modulating the concentration, localization, stability, and/or activity of the thresholding polypeptide. The tuner polypeptide can be capable of diminishing the concentration, stability, and/or activity of the thresholding polypeptide. For example, the tuner polypeptide can comprise a first thresholding protease. The first thresholding protease in a first thresholding protease active state can be capable of cutting a first thresholding protease cut site of the thresholding polypeptide. The third partner domain can comprise the first thresholding protease cut site. The thresholding polypeptide can comprise a degron. The first thresholding protease in the first thresholding protease active state can be capable of cutting the first thresholding protease cut site of the thresholding polypeptide to expose the degron. The degron of the thresholding polypeptide being exposed can change the thresholding polypeptide to a thresholding polypeptide destabilized state.

In some embodiments provided herein, the thresholding module design is based on the Cfa split intein system. Cfa provides modular domains that can undergo reversible protein dimerization and irreversible protein splicing (Stevens et al, JACS 2016). The Cfa intein has two separate translated polypeptides, CfaN and CfaC. When fused with extein protein domains, CfaN and CfaC can reversibly dimerize. In the dimeric form, the CfaN and CfaC can irreversibly excise themselves and thereby splice the exteins together to form a single spliced protein. A truncated variant of CfaN, CfaN2, lacks an essential domain for irreversible protein splicing, but can still reversibly dimerize with CfaC. To introduce a thresholding effect, the synthetic protein circuit can comprise, in addition to two input species, a third species (e.g., a thresholding species, a decoy) engineered by fusing CfaN with the N-terminal half of a catalytically dead TVMVP mutant, nTVMVPmut-CfaN. This component can undergo irreversible protein splicing with CfaC-cTVMVP to form a catalytically inactive TVMVP. The irreversibility of this reaction can provide a flux of input protein into inactive components that do not further affect the system. In this way, the thresholding species (nTVMVPmut-CfaN) and part of the input (CfaC-cTVMVP) mutually annihilate one another, approximately subtracting a fixed amount of one input species (CfaC-cTVMVP), and thereby introducing a thresholding effect into the system whose magnitude can be controlled by modulating the concentration or expression of nTVMVPmut-CfaN.

FIG. 1A depicts a non-limiting exemplary embodiment of a synthetic protein circuit provided herein. A first input polypeptide 102 can comprise a first polypeptide domain 104 (e.g., a first TEV protease halve) and a first partner domain 106 (e.g., a truncated split intein N-fragment). A second input polypeptide 108 can comprise a second polypeptide domain 110 (e.g., a second TEV protease halve) and a second partner domain 112 (e.g., a split intein C-fragment). A thresholding polypeptide 114 (e.g., a decoy) can comprise a third polypeptide domain 116 comprising a variant of first polypeptide domain 104 (e.g., a first TEV protease halve comprising inactivating mutation(s)). The thresholding polypeptide 114 can comprise a third partner domain 118 (e.g., a split intein N-fragment). The thresholding polypeptide 114 can comprise a first thresholding protease cut site 120 that a first thresholding protease in a first thresholding protease active state is capable of cutting. The first thresholding protease cut site 120 can be located in the third partner domain 118. The thresholding polypeptide 114 can comprise a fourth partner domain 122 (e.g., a heterodimerizing leucine zipper). A tuner polypeptide 124 can comprise a fifth partner domain 130 (e.g., a heterodimerizing leucine zipper) capable of binding the fourth partner domain 122. The tuner polypeptide can be capable of diminishing the concentration, stability, and/or activity of the thresholding polypeptide. The tuner polypeptide can be capable of modulating the location of the thresholding polypeptide (e.g., sequestering the thresholding polypeptide). The tuner polypeptide 124 can comprise a first part and a second part of a first thresholding protease 126 (e.g., TMVM) capable of associating with each other to constitute a first thresholding protease in a first thresholding protease active state, wherein the first thresholding protease in a first thresholding protease active state is capable of cutting the first thresholding protease cut site 120 of the thresholding polypeptide 114. The tuner polypeptide 124 can comprise one or more cut sites 128 for a sixth protease.

The first partner domain 106 can be capable of binding the second partner domain 112 to form transient complex 132. The first polypeptide domain and the second polypeptide domain can be capable of associating with each other within transient complex 132 to constitute a first protein (e.g., TEV protease, a fifth protease) capable of being in a first protein active state. The first partner domain 106 can bind the second partner domain 112 reversibly. In some embodiments, the second partner domain 112 comprises a split intein C-fragment and the first partner domain 106 comprises a split intein N-fragment variant (e.g., a truncated variant of CfaN lacking an essential domain for irreversible protein splicing). The binding of the first partner domain 106 and the second partner domain 112 can be incapable of inducing trans-splicing the first input polypeptide 102 and the second input polypeptide 108. The transient complex 132 comprising the first protein in the first protein active state can be capable of generating a product in a first enzymatic reaction (e.g., a proteolytic reaction) with a substrate 134. The substrate 134 can comprise a cut site 136 the first protein (e.g., fifth protease) in the first protein active state is capable of cutting. The transient complex 132 comprising the first protein (e.g., fifth protease) in the first protein active state can be capable of cutting the cut site 136 of substrate 134 (and thereby generating a product). In some embodiments, the substrate 134 can change from an inactive state to an active state (e.g., a fluorescent state) when the transient complex 132 comprising a first protein in the first protein active state cuts the cut site 136 of the substrate. In some embodiments, the substrate 134 can comprise a degron 138. In some such embodiments, cutting the cut site 136 of substrate 134 can expose the degron 138. The degron 138 of the substrate 134 being exposed can change the substrate to a substrate destabilized state.

The third partner domain 118 can be capable of binding the second partner domain 112, generating intermediate 140. Intermediate 140 can comprise an intein intermediate. In some embodiments, the first protein is not in the first protein active state when the third partner domain 118 binds the second partner domain 112. Intermediate 140 can comprise the first protein in a first protein inactive state. Intermediate 140 can be incapable of catalyzing the first enzymatic reaction with substrate 134. In some embodiments, the second partner domain 112 comprises a split intein C-fragment (e.g., CfaC) and the third partner domain 118 comprises a split intein N-fragment (e.g., CfaN). The third partner domain 118 and the second partner domain 112 can be capable of inducing trans-splicing of the thresholding polypeptide 114 and second input polypeptide 108 when the second partner domain 112 binds the third partner domain 118, thereby generating a conjugate 142 comprising the first polypeptide domain 104 and the third polypeptide domain 116. The conjugate 142 can be incapable of being in the first protein active state. The conjugate 142 can be incapable of catalyzing the first enzymatic reaction with substrate 134. The trans-splicing reaction can also generate an intein conjugate 144 comprising the second partner domain 112 and the third partner domain 118.

Figure 1B:
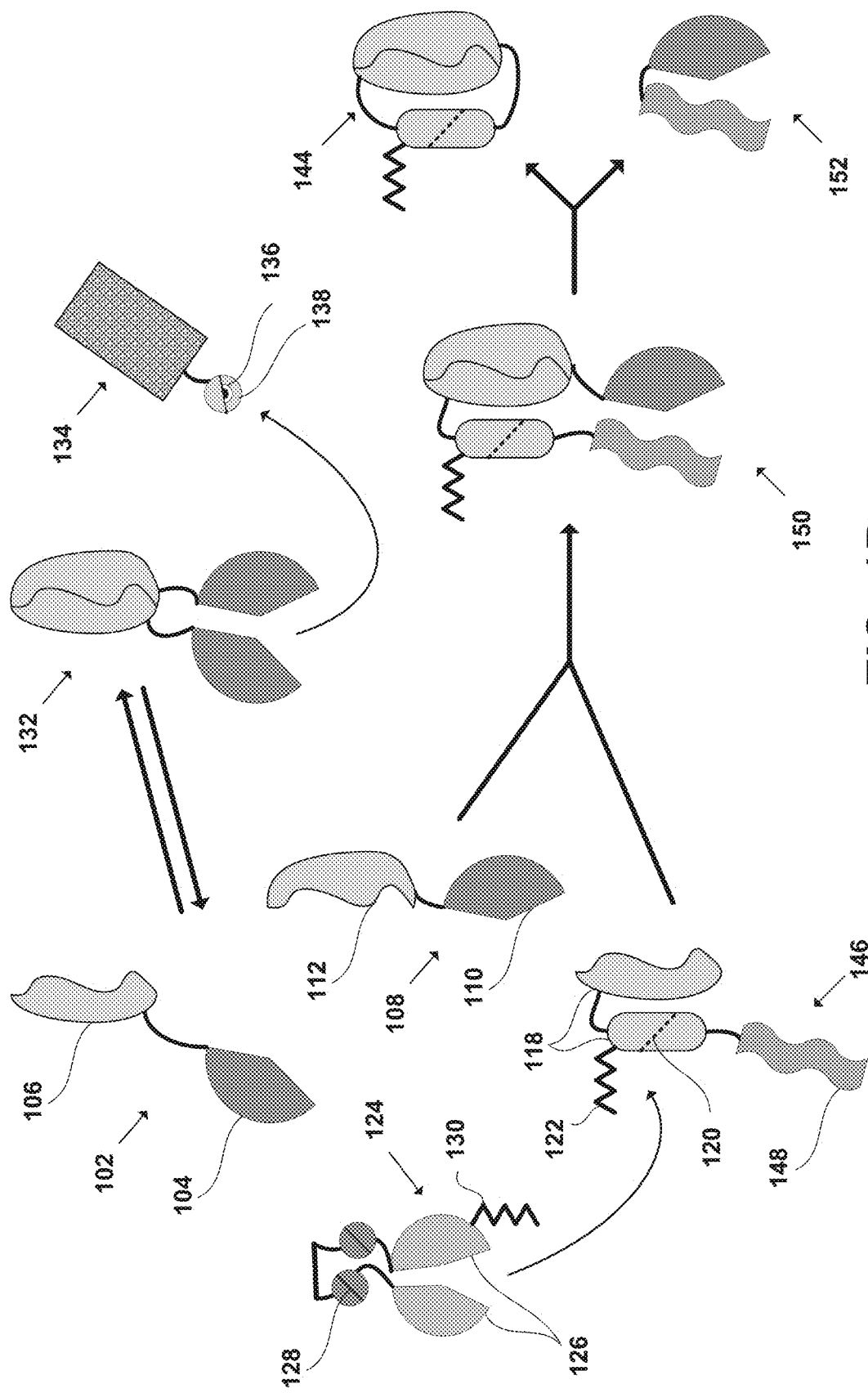

FIG. 1B depicts a non-limiting exemplary embodiment of a synthetic protein circuit provided herein. A thresholding polypeptide 146 (e.g., a decoy) can comprise a third polypeptide domain 148 that is non-homologous to the first polypeptide domain 104 and a third partner domain 118 (e.g., a split intein N-fragment). The third partner domain 118 can be capable of binding the second partner domain 112, generating intermediate 150. Intermediate 150 can comprise an intein intermediate. In some embodiments, the first protein is not in the first protein active state when the third partner domain 118 binds the second partner domain 112. Intermediate 150 can comprise the first protein in a first protein inactive state. Intermediate 150 can be incapable of catalyzing the first enzymatic reaction with substrate 134. In some embodiments, the second partner domain 112 comprises a split intein C-fragment (e.g., CfaC) and the third partner domain 118 comprises a split intein N-fragment (e.g., CfaN). The third partner domain 118 and the second partner domain 112 can be capable of inducing trans-splicing of the thresholding polypeptide 114 and second input polypeptide 108 when the second partner domain 112 binds the third partner domain 118, thereby generating a conjugate 152 comprising the first polypeptide domain 104 and the third polypeptide domain 148. The conjugate 152 can be incapable of being in the first protein active state. The conjugate 152 can be incapable of catalyzing the first enzymatic reaction with substrate 134. The trans-splicing reaction can also generate an intein conjugate 144 comprising the second partner domain 112 and the third partner domain 118.

Figure 1C:
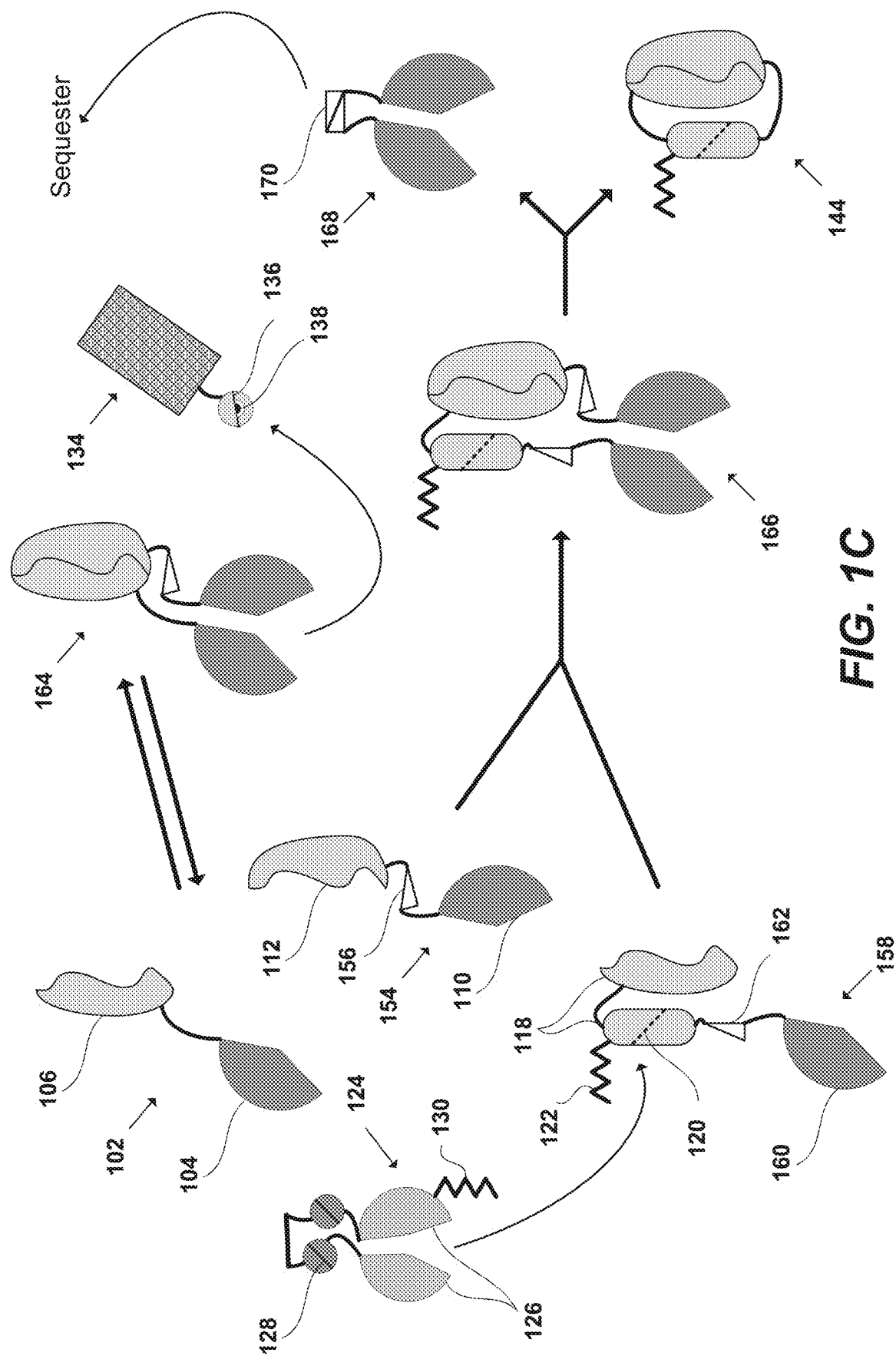

FIG. 1C depicts a non-limiting exemplary embodiment of a synthetic protein circuit provided herein. The second input polypeptide 154 can comprise a first half of an elimination site 156 adjacent to the second partner domain 112. The thresholding polypeptide 158 (e.g., a decoy) can comprise a third polypeptide domain 160. Third polypeptide domain 160 can be homologous or nonhomologous to the first polypeptide domain 104. The thresholding polypeptide 158 can comprise a second half of an elimination site 162 adjacent to the third partner domain 118. The transient complex 164 can form and behave as discussed above regarding transient complex 132. The third partner domain 118 can be capable of binding the second partner domain 112, generating intermediate 166. Intermediate 166 can comprise an intein intermediate. In some embodiments, the first protein is not in the first protein active state when the third partner domain 118 binds the second partner domain 112. Intermediate 166 can comprise the first protein in a first protein inactive state. Intermediate 166 can be incapable of catalyzing the first enzymatic reaction with substrate 134. In some embodiments, the second partner domain 112 comprises a split intein C-fragment (e.g., CfaC) and the third partner domain 118 comprises a split intein N-fragment (e.g., CfaN). The third partner domain 118 and the second partner domain 112 can be capable of inducing trans-splicing of the thresholding polypeptide 158 and second input polypeptide 154 when the second partner domain 112 binds the third partner domain 118, thereby generating a conjugate 168 comprising the first polypeptide domain 104 and the third polypeptide domain 160. The conjugate 168 can be incapable of being in the first protein active state. The conjugate 168 can be incapable of catalyzing the first enzymatic reaction with substrate 134. The conjugate 168 can comprise an intact elimination site 170. The intact elimination site 170 can comprise a localization sequence (e.g., a nuclear localization signal, a nuclear export signal). The intact elimination site 170 can be capable of inducing the sequestering of the conjugate (e.g., inducing the transport of the conjugate to a portion of the cell where the first enzymatic reaction cannot occur). The trans-splicing reaction can also generate an intein conjugate 144 comprising the second partner domain 112 and the third partner domain 118.

Figure 1D:
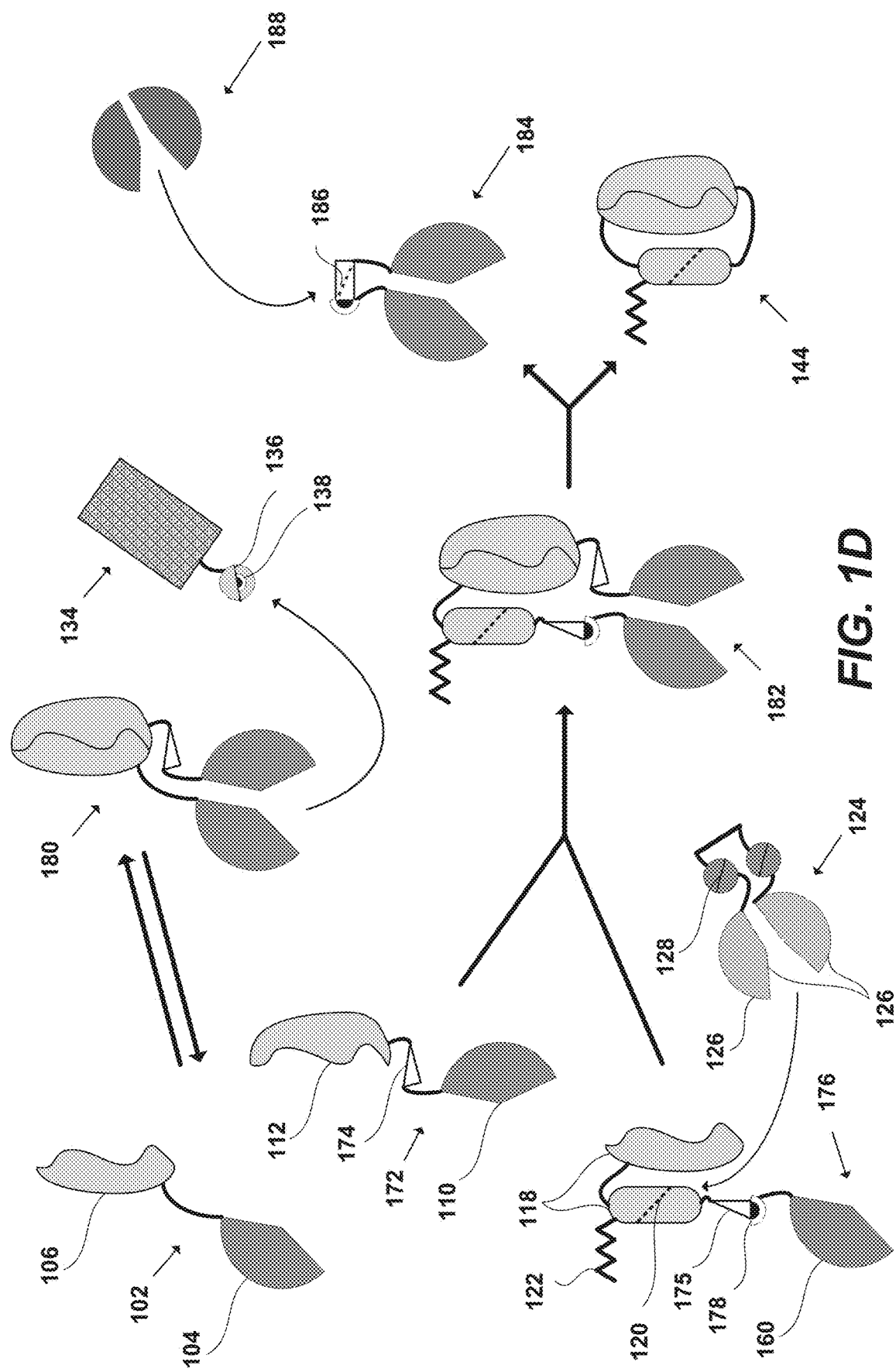

FIG. 1D depicts a non-limiting exemplary embodiment of a synthetic protein circuit provided herein. The second input polypeptide 172 can comprise a first half of an elimination site 174 adjacent to the second partner domain 112. The thresholding polypeptide 176 (e.g., a decoy) can comprise a third polypeptide domain 160. Third polypeptide domain 160 can be homologous or nonhomologous to the first polypeptide domain 104. The thresholding polypeptide 176 can comprise a second half of an elimination site 175 adjacent to the third partner domain 118. The thresholding polypeptide 176 can comprise a degron 178 adjacent to the second half of the elimination site 175. The transient complex 180 can form and behave as discussed above regarding transient complex 132. The third partner domain 118 can be capable of binding the second partner domain 112, generating intermediate 182. Intermediate 182 can comprise an intein intermediate. In some embodiments, the first protein is not in the first protein active state when the third partner domain 118 binds the second partner domain 112. Intermediate 182 can comprise the first protein in a first protein inactive state. Intermediate 182 can be incapable of catalyzing the first enzymatic reaction with substrate 134. In some embodiments, the second partner domain 112 comprises a split intein C-fragment (e.g., CfaC) and the third partner domain 118 comprises a split intein N-fragment (e.g., CfaN). The third partner domain 118 and the second partner domain 112 can be capable of inducing trans-splicing of the thresholding polypeptide 176 and second input polypeptide 172 when the second partner domain 112 binds the third partner domain 118, thereby generating a conjugate 184 comprising the first polypeptide domain 104 and the third polypeptide domain 176. The conjugate 184 can be incapable of being in the first protein active state. The conjugate 184 can be incapable of catalyzing the first enzymatic reaction with substrate 134. The conjugate 184 can comprise an intact elimination site 186. The intact elimination site 186 can comprise a second thresholding protease cut site that a second thresholding protease 188 in a second thresholding protease active state is capable of cutting. In some such embodiments, second thresholding protease 188 cutting the intact elimination site 186 of conjugate 184 can expose the degron 178. The degron 178 of the conjugate 184 being exposed can change the conjugate to an conjugate destabilized state. The trans-splicing reaction can also generate an intein conjugate 144 comprising the second partner domain 112 and the third partner domain 118.

Figure 2A:
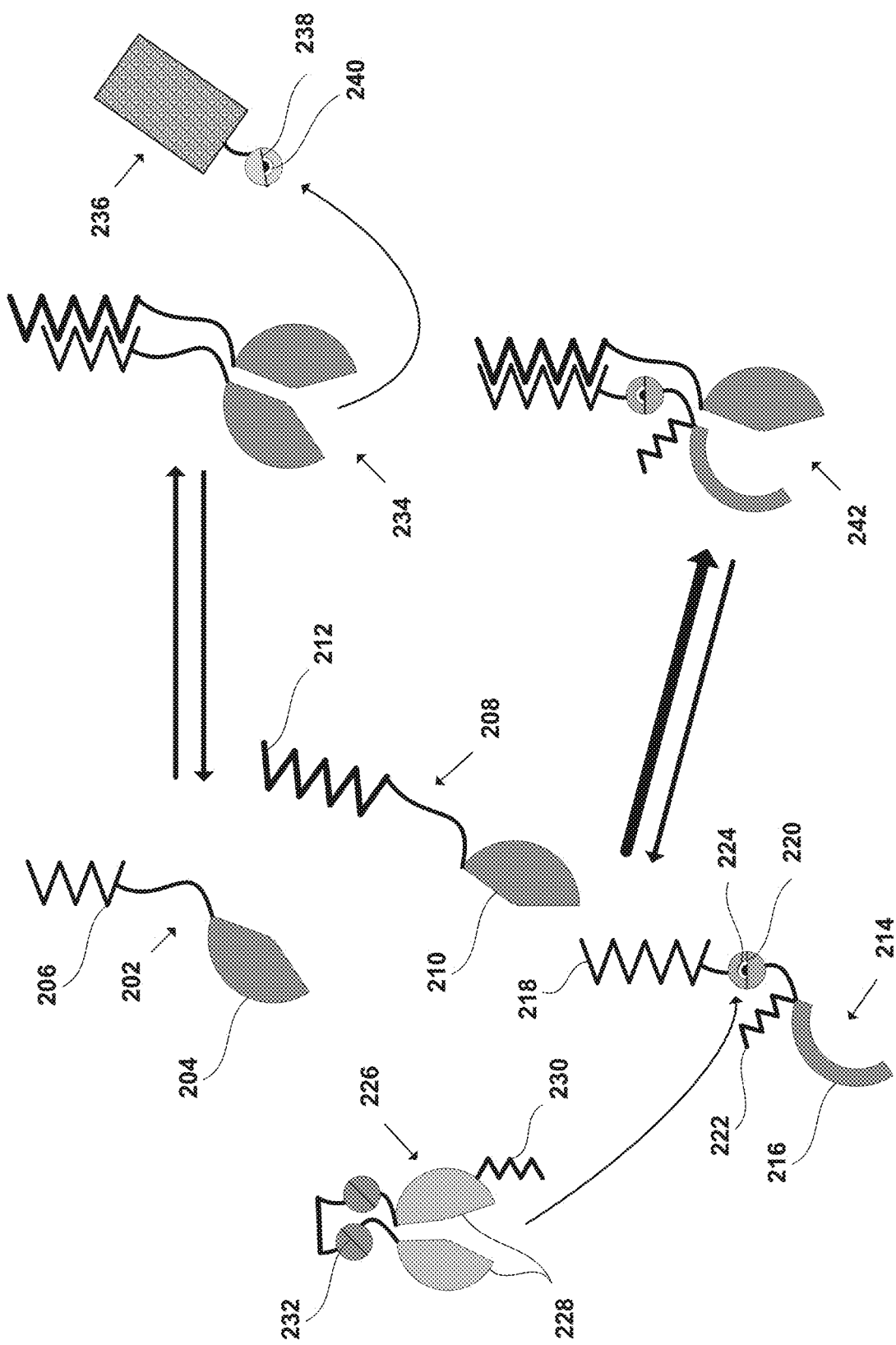
FIGS. 2A-2B show non-limiting exemplary schematic illustrations of synthetic protein circuits provided herein.

FIG. 2A depicts a non-limiting exemplary embodiment of a synthetic protein circuit provided herein. A first input polypeptide 202 can comprise a first polypeptide domain 204 (e.g., a first TEV protease halve) and a first partner domain 206 (e.g., a heterodimerizing leucine zipper). A second input polypeptide 208 can comprise a second polypeptide domain 210 (e.g., a second TEV protease halve) and a second partner domain 212 (e.g., a heterodimerizing leucine zipper). A thresholding polypeptide 214 (e.g., a decoy) can comprise third polypeptide domain 216 comprising a variant of first polypeptide domain 204 (e.g., a first TEV protease halve comprising inactivating mutation(s)). The thresholding polypeptide 214 can comprise a third partner domain 218 (e.g., a heterodimerizing leucine zipper). The thresholding polypeptide 214 can comprise a first thresholding protease cut site 220 that a first thresholding protease in a first thresholding protease active state is capable of cutting. The first thresholding protease cut site 220 can be located in the third partner domain 218 or within another portion of thresholding polypeptide 214. The thresholding polypeptide 214 can comprise a fourth partner domain 222 (e.g., a heterodimerizing leucine zipper). The thresholding polypeptide 214 can comprise a degron 224. A tuner polypeptide 226 can comprise a fifth partner domain 230 (e.g., a heterodimerizing leucine zipper) capable of binding the fourth partner domain 222. The tuner polypeptide can be capable of diminishing the concentration, stability, and/or activity of the thresholding polypeptide. The tuner polypeptide can be capable of modulating the location of the thresholding polypeptide (e.g., sequestering the thresholding polypeptide). The tuner polypeptide 226 can comprise a first part and a second part of a first thresholding protease 228 (e.g., TMVM) capable of associating with each other to constitute a first thresholding protease in a first thresholding protease active state, wherein the first thresholding protease in a first thresholding protease active state is capable of cutting the first thresholding protease cut site 220 of the thresholding polypeptide 214. In some embodiments, cutting the first thresholding protease cut site 220 of the thresholding polypeptide 214 can expose the degron 224. The degron 224 of the thresholding polypeptide 214 being exposed can change the thresholding polypeptide to a thresholding polypeptide destabilized state. The tuner polypeptide 226 can comprise one or more cut sites 232 for a sixth protease.

The first partner domain 206 can be capable of binding the second partner domain 212 to form transient complex 234. The first polypeptide domain and the second polypeptide domain can be capable of associating with each other within transient complex 234 to constitute a first protein (e.g., TEV protease, a fifth protease) capable of being in a first protein active state. The first partner domain 206 can bind the second partner domain 212 reversibly. The first partner domain 206 can bind the second partner domain 212 with a first binding affinity. The transient complex 234 comprising the first protein in the first protein active state can be capable of generating a product in a first enzymatic reaction (e.g., a proteolytic reaction) with a substrate 236. The substrate 236 can comprise a cut site 238 the first protein (e.g., fifth protease) in the first protein active state is capable of cutting. The transient complex 234 comprising the first protein (e.g., fifth protease) in the first protein active state can be capable of cutting the cut site 238 of substrate 236 (and thereby generating a product). In some embodiments, the substrate 236 can change from an inactive state to an active state (e.g., a fluorescent state) when the transient complex 234 comprising a first protein in the first protein active state cuts the cut site 238. In some embodiments, the substrate 236 can comprise a degron 240. In some such embodiments, cutting the cut site 238 of substrate 236 can expose the degron 240. The degron of the substrate 236 being exposed can change the substrate to a substrate destabilized state.

The third partner domain 218 can be capable of binding the second partner domain 212, generating complex 242. The third partner domain 218 can bind the second partner domain 212 reversibly or irreversibly. The third partner domain 218 can bind the second partner domain 212 with a second binding affinity. The second binding affinity can be at least 1.1-greater than the first binding affinity. The first partner domain can comprise one or mutations decreasing binding affinity for the second partner domain. In some embodiments, the first protein is not in the first protein active state when the third partner domain 218 binds the second partner domain 212. Complex 242 can comprise the first protein in a first protein inactive state. Complex 242 can be incapable of catalyzing a first enzymatic reaction (e.g., a proteolytic reaction) with substrate 236.

Figure 2B:
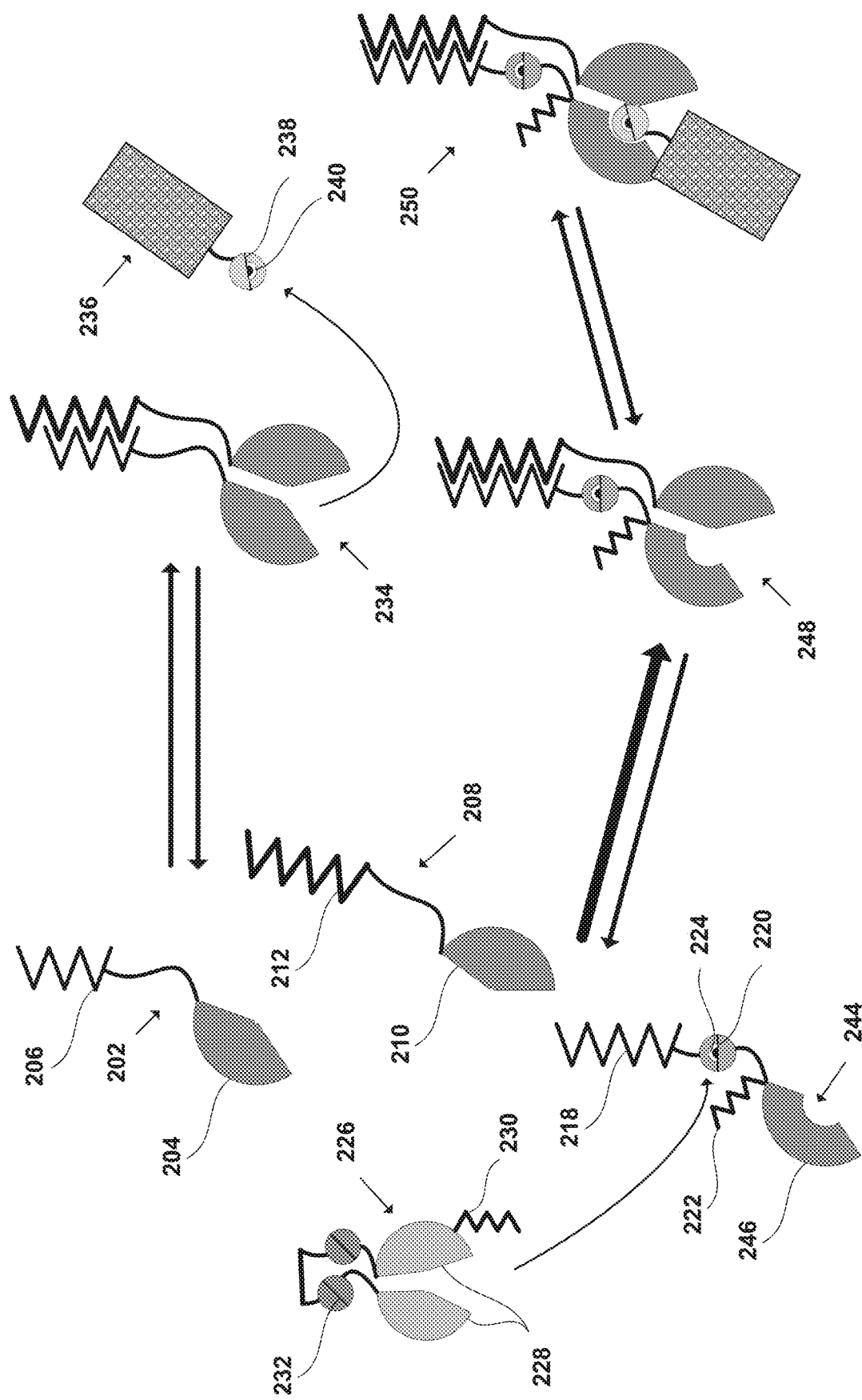

FIG. 2B depicts a non-limiting exemplary embodiment of a synthetic protein circuit provided herein. A thresholding polypeptide 244 (e.g., a decoy) can comprise third polypeptide domain 246 comprising a dominant negative variant of first polypeptide domain 204. The third partner domain 218 can be capable of binding the second partner domain 212, generating complex 248. The third partner domain 218 can bind the second partner domain 212 reversibly or irreversibly. The third partner domain 218 can bind the second partner domain 212 with a second binding affinity. The second binding affinity can be at least 1.1-greater than the first binding affinity. The first partner domain can comprise one or mutations decreasing binding affinity for the second partner domain. In some embodiments, the first protein is not in the first protein active state when the third partner domain 218 binds the second partner domain 212. Complex 248 can comprise the first protein in a first protein inactive state. Complex 248 can be incapable of catalyzing the first enzymatic reaction with substrate 236. Complex 248 can be capable of binding substrate 236 to form sink complex 250. Complex 248 can be bind substrate 236 reversibly or irreversibly. The formation of sink complex 250 can reduce or prevent catalysis of substrate 236 by a first protein in a first protein active state while substrate 236 is a component of sink complex 250.

The thresholding compositions and methods described herein do not require any other factors and therefore should apply to other enzymes (e.g., proteases) in diverse cell types, including prokaryotes as well as eukaryotes. The thresholding compositions and methods described herein are also compatible with alternative dimerization domains, including other split inteins (e.g. Npu (Stevens et al, JACS 2016)), heterodimerizing leucine zippers with varied affinities (Reinke et al, JACS 2010), or other heterodimerizing protein domains with different affinities (Chen et al, Nat. Biotech. 2008). Some embodiments of the synthetic protein circuits provided herein are described and validated with a protease output. However, the novel thresholding circuit design disclosed herein can be used to control any protein activity, such as those that for which a protein of interest can (1) be successfully split and reconstituted and/or (2) one can identify an inactivating mutation in the protein. Kinases and phosphatases have been shown to meet these conditions (K. Camacho-Soto et al, JACS 2014), as has Cas9 (Zetsche et al, Nat. Biotech. 2015), as well as a growing list of diverse proteins (Dagliyan et al, Nat. Comm. 2018). In contrast to previous efforts by Gramespacher et al conditionally reconstituting TEV protease activity by protein splicing (Gramespacher et al, JACS 2017), the compositions and methods provided herein employ protein splicing to deactivate proteases, thereby reducing their activity below a threshold. There are provided methods, compositions, and systems for engineering proteins (e.g., proteases) to regulate one another and/or target proteins. The methods provided herein enable engineering and thresholding of circuits that perform regulatory cascades, binary logic computations, analog band-pass signal processing, generation of dynamic behaviors such as pulsing, coupling to endogenous cellular states such as oncogene activation, and/or the ability to control cellular behaviors such as apoptosis. The flexibility and scalability of the compositions and methods provided herein enable it to be reconfigured to implement a broad range of additional functions in some embodiments. The circuits can also be encoded and delivered to cells in multiple formats, including DNA, RNA, and at the protein level itself, enabling versatile applications with or without genomic integration or mutagenesis.

Recent work by the Applicant established a system for designing and constructing protein-level circuits out of modified viral proteases. These circuits can sense cell states, process information, and actuate cellular responses such as cell death (Gao, Xiaojing J., et al, Science 2018). This system was termed CHOMP (Circuits of Hacked Orthogonal Modular Proteases). The protein level circuit module disclosed herein can be incorporated into larger synthetic protein circuits such as those based on CHOMP to provide thresholding capabilities. The synthetic protein circuits provided herein can employ CHOMP components and/or design concepts as well as can be situated within a larger circuit comprising CHOMP protein circuit(s). The synthetic protein circuits provided herein can be configured in a variety of ways. In some embodiments, the synthetic protein circuit includes a first protease, second protease, third protease, fourth protease, fifth protease, sixth protease, seventh protease, eighth protease, ninth protease and/or tenth protease. Any of said proteases may comprise or be composed of a compound protease as described herein. In some embodiments, the compound protease comprises a protease domain with a cut site for another protease, wherein the compound protease is deactivated by cleavage of cut site for the other protease. In some embodiments, the compound protease is activated or deactivated by another protease, thereby forming a protein circuit. The protein circuits may be programmable with different variations on the proteases and their targets to, for example, perform logic gate functions, or be part of bandpass or adaptive pulse circuits. As described herein, a "cut site" is a peptide sequence specific for one or more proteases that when recognized or bound by the one or more proteases are cleaved by the one or more proteases. The peptide sequence of the cut site may be specific for one protease or a type of proteases, or may be general to multiple proteases or types of proteases.

As described herein, a "compound protease" refers to a protease with at least two parts of a protease domain. The parts may be linked together by one or more cut sites such as a cut site specific for another protease. The parts of the protease domain may but need not be separate subunits of the protease, or may include separate portions of a peptide or peptides that makes up the protease. As described herein, a "protease domain" includes one or more peptides that when associated together have protease activity. For example, the protease activity may be the ability to cleave another peptide. In some embodiments, the compound protease comprises or consists of a tobacco etch virus NIa (TEV) protease, tobacco vein mottling virus (TVMV) NIa protease, sugarcane mosaic virus NIa protease, sunflower mild mosaic virus NIa protease, turnip mosaic virus NIa protease, plum pox virus NIa protease, soybean mosaic virus protease, hepatitis c virus (HCV) ns3 protease, hepatitis a virus 3c protease, dengue virus NS3 protease, zika virus NS3 protease, yellow fever virus NS3 protease, or human herpes virus 1 protease. In some embodiments, the compound protease comprises or consists of a human site-specific protease such as thrombin and/or enteropeptidase. Some embodiments of the proteases described herein include one or more linkers or linker peptides. The linkers or linker peptides may connect or link (directly or indirectly, and/or covalently or noncovalently) various parts of the protease such as a cut site or a part of the cut site to a protease domain or a part of a protease domain. However, this disclosure is not limited to only linkers or linker peptides connecting the protease parts. Examples of a linker is a peptide that includes 1-10, 10-25, 25-50, 50-100, or 100-1000 amino acids.

Some embodiments of the compound protease include an association domain. Association domains can comprise partner domains as described herein. The association domain can include two parts each binding together noncovalently to ultimately link the first and second parts of the protease domain a together. Examples of association domains include a leucine zipper motif or a complementary leucine zipper motif, a scaffold protein or a fragment thereof, a scaffold-binding motif, an antibody, an epitope, tetratricopeptide repeat, a tetracopeptide repeat-binding motif, a G-protein-coupled receptor, a β-arrestin, and/or a G protein. In some embodiments, the association domain includes any protein(s) or component(s) of protein(s) that bind together. Thus, the association domain is contemplated to cover any protein-protein interaction according to some embodiments. In some embodiments, the association domain includes a ligand-binding protein or domain and/or the ligand.

Some embodiments include the use of degrons. Examples of degrons include a portion of a protein that affect the regulation of protein degradation rates. Some degrons are ubiquitin-dependent or ubiquitin-independent. me embodiments include the use of degrons. Examples of degrons include a portion of a protein that affect the regulation of protein degradation rates. Some degrons are ubiquitin-dependent or ubiquitin-independent. In some embodiments of the compound protease, the compound protease includes a degron. In some embodiments, the compound protease includes multiple degrons. In some embodiments, at least one degron of the compound protease destabilizes the compound protease when present on the compound protease by enhancing degradation of the compound protease. In some embodiments, at least one of the degrons of the compound protease is or comprises a conditional N-end degron. In some such embodiments, the at least one degron or the condition N-end degron does not inactivate or destabilize the compound protease until the degron or a component thereof is cleaved by another protease to reveal the degron and allow it to stabilize the compound protease. In some embodiments, one or more degrons of the compound protease comprise a conditional N-end degron such as an N-end degron that is conditional on cleavage of a cut site specific for an enzyme, a second protease, or the compound protease, on the compound protease. As used herein, "stabilize" may refer to the ability of a peptide or molecule to maintain the same or another molecule or peptide in a particular state such as an active conformation. "Stabilize" may also refer to the ability of a peptide or molecule to prevent or decrease the amount of degradation that the same or another molecule or peptide faces. As used herein, "destabilize" may refer to the ability of a peptide or molecule to prevent or stop the same or another molecule or peptide from maintaining a particular state. "Destabilize" may also refer to the ability of a peptide or molecule to allow or increase the amount of degradation that the same or another molecule or peptide faces, such as by increasing the affinity of the same or other molecule or peptide to a digestive protein.

Thresholding Synthetic Protein Circuits Wherein Partner Domains Comprise Signal Transducer Binding Domains Disclosed herein include synthetic protein circuits. In some embodiments, the synthetic protein comprises: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the first input polypeptide and the third input polypeptide are in close proximity. In some embodiments, the synthetic protein comprises: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the second input polypeptide and the third input polypeptide are in close proximity.

The thresholding synthetic protein circuits provided herein can situated into a larger synthetic protein circuit comprising one or more synthetic protein circuit design components and/or concepts of U.S. application Ser. No. 16/556,063, filed on Aug. 29, 2019, the content of which is incorporated herein by reference in its entirety. In some embodiments, the thresholding synthetic protein circuits provided herein can comprise one or more synthetic protein circuit design components and/or concepts of U.S. application Ser. No. 16/556,063. The first partner domain, second partner domain, and/or third partner domain comprise a signal transducer binding domain. The signal transducer binding domain can be capable of binding to a signal transducer in a signal transducer active state or in a signal transducer inactive state. For example, the first partner domain, second partner domain, and/or third partner domain can comprise a RAS binding domain (RBD) and/or RAS association domain (RAD). The first partner domain can comprise a first signal transducer binding domain. The second partner domain can comprise a second signal transducer binding domain. The third partner domain can comprise a third signal transducer binding domain.

The first signal transducer binding domain, second signal transducer binding domain and/or the third signal transducer binding domain can be identical. The first signal transducer binding domain, second signal transducer binding domain and/or the third signal transducer binding domain can be different. The first signal transducer binding domain, second signal transducer binding domain and/or the third signal transducer binding domain can bind a first signal transducer in an active and/or inactive state. The first signal transducer binding domain, second signal transducer binding domain and/or the third signal transducer binding domain can bind a second signal transducer in an active and/or inactive state. The first transducer and the second transducer can be identical or different.

The first signal transducer, the second signal transducer, or both, can be capable of being localized at an association location. In some embodiments, the first signal transducer, the second signal transducer, or both, are localized at an association location. The first signal transducer when in a first signal transducer active state, the second signal transducer when in a second signal transducer active state, or both, can be capable of being localized at the association location. In some embodiments, the first signal transducer when in a first signal transducer active state, the second signal transducer when in a second signal transducer active state, or both, are localized at the association location. The first signal transducer when in a first inactive state, the second signal transducer when in a second inactive state, or both, can be capable of being localized at the association location. In some embodiments, the first signal transducer when in a first inactive state, the second signal transducer when in a second inactive state, or both, localizes at the association location. The association location can comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof. The association location can comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

Signal Transducers

A variety of signal transducers are contemplated herein. The first signal transducer can be capable of binding the first signal transducer binding domain and/or the second signal transducer can be capable of binding the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof. The first signal transducer, the second signal transducer, or both can be endogenous proteins. The first signal transducer, the second signal transducer, or both comprise AKT, PI3K, MAPK, p44/42 MAP kinase, TYK2, p38 MAP kinase, PKC, PKA, SAPK, ELK, INK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCγ, NF-kB, FAK, CREB, αIIIβ3, FcεRI, BAD, p70S6K, STAT1, STAT2, STAT3, STAT5, STAT6, or any combination thereof.

The first signal transducer and/or the second signal transducer can be capable of regulating cell survival, cell growth, cell proliferation, cell adhesion, cell migration, cell metabolism, cell morphology, cell differentiation, apoptosis, or any combination thereof. The first signal transducer, the second signal transducer, or both can comprise a RAS protein (e.g., KRAS, NRHAS, HRAS). The first signal transducer, the second signal transducer, or both can be exogenous proteins. In some embodiments, the synthetic protein circuit comprises the first signal transducer, the second signal transducer, or both. In some embodiments, the first signal transducer, the second signal transducer, or both comprise a lipid (e.g., a phospholipid, phosphatidylinositol 3-phosphate).

Signal transducers can be can be associated with one or more diseases or disorders. In some embodiments, a disease or disorder is characterized by an aberrant signaling of one or more signal transducers disclosed herein. In some embodiments, the activation level of the signal transducer correlates (e.g., positively correlates) with the occurrence and/or progression of a disease or disorder. The activation level of the signal transducer can be directly responsible or indirectly responsible for the etiology of the disease or disorder. Non-limiting examples of signal transducers, signal transduction pathways, and diseases and disorders characterized by aberrant signaling of said signal transducers are listed in Tables 1-3 of U.S. application Ser. No. 16/556,063, filed on Aug. 29, 2019, the content of which is incorporated herein by reference in its entirety.

Signal Transducer Binding Domains

There are provided, in some embodiments, first signal transducer binding domains, second signal transducer binding domains, and/or third signal transducer binding domains. Two or more of the first signal transducer binding domain, the second signal transducer binding domain, and/or third signal transducer binding domain can be identical. Two or more of the first signal transducer binding domain, the second signal transducer binding domain, and/or third signal transducer binding domain can be different. The first signal transducer binding domain, the second signal transducer binding domain, and/or third signal transducer binding domain each can be capable of binding molecules of the first signal transducer and/or the second signal transducer. The third signal transducer binding domain can be capable of binding to a third signal transducer at the association location. In some embodiments, the first signal transducer, the second signal transducer, and/or the third signal transducer belong to a signal transduction pathway.

The first signal transducer binding domain, the second signal transducer binding domain, and/or the third signal transducer binding domain can comprise a RAS binding domain (RBD) and/or RAS association domain (RAD). In some embodiments, the first signal transducer binding domain, the second signal transducer binding domain, and/or the third signal transducer binding domain comprises a lipid binding domain (e.g., a Pleckstrin homology (PH) domain). The first signal transducer binding domain, the second signal transducer binding domain, and/or the third signal transducer binding domain can comprise a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

There are provided, in some embodiments, antigen-binding moieties (e.g., monobodies). In some embodiments, first signal transducer binding domain, the second signal transducer binding domain, and/or third signal transducer binding domain comprise an antigen binding moiety. The antigen-binding moiety can be configured to bind any of the signal transducers contemplated herein. The antigen-binding moiety can be configured to bind a signal transducer in an active and/or inactive state as described herein.

Antigen-binding moieties can comprise antibodies, antibody fragments, and variants. In some embodiments, antibody fragments and variants may comprise antigen binding regions from intact antibodies. Examples of antibody fragments and variants may include, but are not limited to Fab, Fab', F(ab')2, and Fv fragments; diabodies; linear antibodies; single-chain antibody molecules such as single chain variable fragment (scFv); and multi specific antibodies formed from antibody fragments.

For the purposes herein, an "antibody" may comprise a heavy and light variable domain as well as an Fc region. As used herein, the term "native antibody" refers to a heterotetrameric glycoprotein of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VT) followed by a number of constant domains. Each light chain has a variable domain at one end (VL) and a constant domain at its other end: the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains comprise hypervariable regions. As used herein, the term "hypervariable region" refers to a region within a variable domain comprising amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody comprising a structure that is complimentary to its target antigen or epitope. Other portions of the variable domain, not interacting with the antigen, are referred to as framework (FVV) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments based on comparisons with other antibodies can also be used. Determining residues that make up CDRs may include the use of numbering schemes including, but not limited to, those taught by Kabai, Chothia, and Honegger.

H and VL domains have three CDRs each. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs has favored canonical structures with the exception of the CDR-H3, which comprises amino acid sequences that may be highly variable in sequence and length between antibodies resulting in a variety of three-dimensional structures in antigen-binding domains. In some cases, CDR-H3s may be analyzed among a panel of related antibodies to assess antibody diversity. Various methods of determining CDR sequences are known in the art and may be applied to known antibody sequences.

As used herein, the term "Fv" refers to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain (to form a single chain Fv (scFv)) or through the introduction of a disulfide bridge between heavy and light chain variable domains.

As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. Using molecular genetics, two scFvs can be engineered in tandem into a single polypeptide, separated by a linker domain, called a "tandem scFv" (tascFv). Construction of a tascFv with genes for two different scFvs yields a "bispecific single-chain variable fragments" (bis-scFvs).

As used herein, the term "bispecific antibody" refers to an antibody capable of binding two different antigens. Such antibodies typically comprise regions from at least two different antibodies. As used herein, the term "diabody" refers to a small antibody fragment with two antigen-binding sites. Diabodies are functional bispecific single-chain antibodies (bscAb). Diabodies comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites.

The term "intrabody" can refer to a form of antibody that is not secreted from a cell in which it is produced, but instead targets one or more intracellular proteins. Intrabodies may be used to affect a multitude of cellular processes including, but not limited to intracellular trafficking, transcription, translation, metabolic processes, proliferative signaling and cell division. In some embodiments, methods provided herein may include intrabody-based therapies. In some such embodiments, variable domain sequences and/or CDR sequences disclosed herein may be incorporated into one or more constructs for intrabody-based therapy.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen.

The modifier "monoclonal" can indicate the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source(s) with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity. In one embodiment, the antibody may be a humanized full-length antibody.

As used herein, the term "antibody variant" refers to a modified antibody (in relation to a native or starting antibody) or a biomolecule resembling a native or starting antibody in structure and/or function (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, IgG1, IgG2, IgG3, IgG4, or IgM), humanized variants, optimized variants, multi-specific antibody variants (e.g., bispecific variants), and antibody fragments.

In some embodiments, the antigen-binding moieties provided herein comprise antibody mimetics (e.g., monobodies). As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (e.g., the protein scaffolds disclosed in U.S. Pat. Nos. 6,673,901 and 6,348,584). In some embodiments, antibody mimetics may be those known in the art including, but are not limited to affibody molecules, affitins, anticalins, avimers, Centyrins, DARPINSTM, Fynomers and Kunitz and domain peptides. In other embodiments, antibody mimetics may include one or more non-peptide regions.

In some embodiments, the antigen-binding moieties provided herein comprise multispecific antibodies that bind more than one epitope. As used herein, the terms "multibody" or "multispecific antibody" refer to an antibody wherein two or more variable regions bind to different epitopes. The epitopes may be on the same or different targets. In some embodiments, a multi-specific antibody is a "bispecific antibody" which recognizes two different epitopes on the same or different antigens. In one aspect, bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

In some embodiments, the antigen-binding moieties provided herein comprise antibodies comprising a single antigen-binding domain (e.g., nanobodies). These molecules are extremely small, with molecular weights approximately one-tenth of those observed for full-sized mAbs. Further antibodies may include "nanobodies" derived from the antigen-binding variable heavy chain regions (VHHs) of heavy chain antibodies found m camels and llamas, which lack light chains (Nelson, A. L., MAbs. 2010. January-February; 2(1):77-83).

In some embodiments, the antibody may be "miniaturized". Among the best examples of mAb miniaturization are the small modular immunopharmaceuticals (SMIPs) from Trubion Pharmaceuticals. These molecules, which can be monovalent or bivalent, are recombinant single-chain molecules containing one VL, one VH antigen-binding domain, and one or two constant "effector" domains, all connected by linker domains. One example of miniaturized antibodies is called "unibody" in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo.

In some embodiments, the antigen-binding moieties provided herein comprise single-domain antibodies (sdAbs, or nanobodies) which are antibody fragment consisting of a single monomelic variable antibody domain. In some embodiments, it is able to bind selectively to a specific antigen (e.g., like a whole antibody). In one aspect, a sdAb may be a "Camel Ig or "camelid VHH". As used herein, the term "camel Ig" refers to the smallest known antigen-binding unit of a heavy chain antibody (Koch-No lte, et al, FASEB J., 2007, 21: 3490-3498). A "heavy chain antibody" or a "camelid antibody" refers to an antibody that contains two VH domains and no light chains (Riechmann L. et al, J. Immunol. Methods, 1999, 231: 25-38; international patent publication NOs. WO 1994/004678 and WO 1994/025591; and U.S. Pat. No. 6,005,079). In another aspect, a sdAb may be a "immunoglobulin new antigen receptor" (IgNAR). As used herein, the term "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulfide bridges, and patterns of intra-loop hydrogen bonds.

In some embodiments, the antigen-binding moieties provided herein comprise intrabodies. Intrabodies are a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. Sequences from donor antibodies may be used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form, a single chain antibody comprising the variable domains of the heavy and light chains joined by a flexible linker polypeptide, intrabodies typically lack disulfide bonds and are capable of modulating the expression or activity of target genes through their specific binding activity. Single chain intrabodies are often expressed from a recombinant nucleic acid molecule and engineered to be retained intracellularly (e.g., retained in the cytoplasm, endoplasmic reticulum, or periplasm).

Partner Domains

The first partner domain, second partner domain, and/or third partner domain can comprise an intein or a fragment thereof. The first partner domain, second partner domain, and/or third partner domain can comprise an split intein or a fragment thereof. An "intein" is a segment of a protein that is able to excise itself and join the remaining portions (the exteins) with a peptide bond in a process known as protein splicing. Inteins are also referred to as "protein introns." The process of an intein excising itself and joining the remaining portions of the protein is herein termed "protein splicing" or "intein-mediated protein splicing." In some embodiments, an intein of a precursor protein (an intein containing protein prior to intein-mediated protein splicing) comes from two genes. Such intein is referred to herein as a split intein. For example, in cyanobacteria, DnaE, the catalytic subunit a of DNA polymerase III, is encoded by two separate genes, dnaE-n and dnaE-c. The intein encoded by the dnaE-n gene is herein referred as "intein-N." The intein encoded by the dnaE-c gene is herein referred as "intein-C." Other intein systems may also be used. For example, a synthetic intein based on the dnaE intein, the Cfa-N and Cfa-C intein pair, has been described (e.g., in Stevens et al., J Am Chem Soc. 2016 Feb. 24; 138(7):2162-5, incorporated herein by reference). Non-limiting examples of intein pairs that may be used in accordance with the present disclosure include: Cfa DnaE intein, Ssp GyrB intein, Ssp DnaX intein, Ter DnaE3 intein, Ter ThyX intein, Rma DnaB intein and Cne Prp8 intein (e.g., as described in U.S. Pat. No. 8,394,604, incorporated herein by reference).

The first partner domain, second partner domain, and/or third partner domain can comprise an intein-N, an intein-C, a fragment thereof, or any combination thereof. For example, the first partner domain, second partner domain, and/or third partner domain can comprise CfaN, CfaC, NpuC, NpuN, gp41-1, gp41-2, gp41-3, gp41-4, gp41-5, gp41-6, gp41-7, gp41-8, IMPDH-1, NrdA-1, NrdA-2, NrdA-4, NrdA-5, NrdA-6, NrdJ-1, NrdJ-2 a fragment thereof, or any combination thereof. The first partner domain can comprise an amino acid sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, identical to SEQ ID NO: 9. The second partner domain can comprise an amino acid sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, identical to SEQ ID NO: 8. The third partner domain can comprise an amino acid sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, identical to any one of SEQ ID NOs: 7, 10, and 11.

The first partner domain can be configured to have a reduced binding affinity for the second partner domain as compared to the binding affinity of the third partner domain for the second partner domain. The first partner domain can comprise at least one amino acid modification, such as a deletion, substitution, addition, or a set of amino acid modifications, that affects binding to the second partner domain. The first partner domain and second partner domain can be homodimers or heterodimers. The fourth partner domain and fifth partner domain can be homodimers or heterodimers.

The binding between the first partner domain and the second partner domain can be reversible. The binding between the third partner domain and the second partner domain can be reversible. The binding between the third partner domain and the second partner domain can be irreversible. In some embodiments, the first partner domain binds the second partner domain with a first binding affinity, and wherein the third partner domain binds the second partner domain with a second binding affinity. The second binding affinity can be equivalent to the first binding affinity. The second binding affinity can be at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) greater than the first binding affinity. The first binding affinity can be at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) greater than the second binding affinity.

The first partner domain can be a variant of the third partner domain that can be configured to reduce the first binding affinity (e.g., the first partner domain comprises one or more mutations as compared to the third partner domain). In some embodiments, the one or more mutations can reduce the first binding affinity by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to the second binding affinity. In some embodiments, the sequence identity between the first partner domain and the third partner domain can be, or be about, 0%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the sequence identity between the first partner domain and the third partner domain can be at least, or at most, 0%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

The first partner domain, second partner domain, third partner domain, fourth partner domain, and/or fifth partner domain can comprise SYNZIP1, SYNZIP2, SYNZIP3, SYNZIP4, SYNZIP5, SYNZIP6, SYNZIP7, SYNZIP8, SYNZIP9, SYNZIP10, SYNZIP11, SYNZIP12, SYNZIP13, SYNZIP14, SYNZIP15, SYNZIP16, SYNZIP17, SYNZIP18, SYNZIP19, SYNZIP20, SYNZIP21, SYNZIP22, SYNZIP23, BATF, FOS, ATF4, BACH1, JUND, NFE2L3, AZip, BZip, or any combination thereof. The first partner domain, second partner domain, third partner domain, fourth partner domain, and/or fifth partner domain can comprise a PDZ domain and/or a PDZ domain ligand. The first partner domain, second partner domain, third partner domain, fourth partner domain, and/or fifth partner domain can comprise an SH3 domain, a PDZ domain, a GTPase binding domain, a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, a bZIP domain, portions thereof, variants thereof, or any combination thereof. The (i) first partner domain and second partner domain, (ii) second partner domain and third partner domain, and/or (iii) fourth partner domain and fifth partner domain, can be a pair of constitutive protein partner domains selected from the group consisting of (a) cognate leucine zipper domains, (b) cognate PSD95-Dlgl-Zo-1 (PDZ) domains, (c) a streptavidin domain and cognate streptavidin binding protein (SBP) domain, (d) a PYL domain and cognate ABI domain, (e) a pair of cognate zinc finger domains, (f) a pair of cognate SH3 domains, and (g) a peptide and antibody or antigen-binding fragment thereof that specifically binds to the peptide. The first partner domain, second partner domain, third partner domain, fourth partner domain, and/or fifth partner domain can comprise CZp, NZp, or any combination thereof.

The third partner domain and the second partner domain can be capable of inducing trans-splicing of the thresholding polypeptide and second input polypeptide when the second partner domain binds the third partner domain, thereby generating a conjugate comprising the second polypeptide domain and the third polypeptide domain. The conjugate can be incapable of being in the first protein active state. The conjugate can be incapable of catalyzing the first enzymatic reaction. The second polypeptide can comprise a first half of an elimination site adjacent to the second partner domain. The thresholding polypeptide can comprise a second half of the elimination site adjacent to the third partner domain. The conjugate can comprise an intact elimination site. The intact elimination site can be capable of inducing the sequestering of the conjugate. The elimination site can comprise a localization signal, such as, for example, a nuclear localization signal (NLS), a nuclear export signal (NES), an endoplasmic reticulum localization sequence, a peroxisome localization sequence, a mitochondrial import sequence, a mitochondrial localization sequence, a cell membrane targeting sequence, a synaptic localization signal, a neuronal axonal localization sequence, a neuronal dendritic localization sequence, or any combination thereof. As used herein, a "localization signal" is a signal, in particular a peptidic signal, which leads to the compartmentalization of the polypeptide carrying it to a particular part of the cell, for example an organelle or a particular topographical localization like the inner or outer face of the cell membrane. The intact elimination site can be capable of destabilizing the conjugate. The elimination site can comprise a second thresholding protease cut site a second thresholding protease in a second thresholding protease active state can be capable of cutting. The second input polypeptide and/or thresholding polypeptide comprise a degron, wherein the conjugate can comprise a degron adjacent to the second thresholding protease cut site. The second thresholding protease in the second thresholding protease active state can be capable of cutting the second thresholding protease cut site of the conjugate to expose the degron. The degron of the conjugate being exposed can change the conjugate to a conjugate destabilized state. There are provided, in some embodiments, degrons. A degron can comprise DI-FR degron, an N-degron, a phospho degron, a heat inducible degron, a photosensitive degron, an oxygen dependent degron, ornithine decarboxylase degron, estrogen receptor domain degrons, an ecDHFR degron, an FKBP degron, a UnaG degron, or any combination thereof. As a non-limiting example, the degron may be an ornithine decarboxylase degron. The degron can comprise an ecDHFR degron.

Thresholding Output

In some embodiments, the first protein in the first protein active state is capable of generating a thresholding output. In some embodiments, the thresholding output comprises a first protein in a first protein active state. In some embodiments, the thresholding output comprises a first enzymatic reaction with a substrate generating a first product. In some embodiments, the third polypeptide domain and the second polypeptide domain are incapable of associating to form the first protein in the first protein active state. In some embodiments, the first protein is a split enzyme. In some embodiments, the first protein is a fusion protein. The first protein can comprise a thresholding output protease. The substrate can comprise a nucleic acid, a protein, a lipid, or any combination thereof. The first protein in a first protein active state can comprise hydrolase activity, transferase activity, lyase activity, isomerase activity, ligase activity, oxidoreductase activity, or any combination thereof. The first protein in a first protein active state can comprise fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. The first protein in a first protein active state can comprise nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof.

The first protein can comprise a polymerase, such as, for example, T7 RNA polymerase, T3 RNA polymerase, SP6 RNA polymerase, RNA polymerase I, RNA polymerase II, RNA polymerase III, RNA polymerase IV, or RNA polymerase V, T7 DNA polymerase, eukaryotic mitochondrial DNA Polymerase γ, prokaryotic DNA polymerase I, prokaryotic DNA polymerase II, prokaryotic DNA polymerase III, prokaryotic DNA polymerase IV, prokaryotic DNA polymerase V, eukaryotic polymerase α, eukaryotic polymerase β, eukaryotic polymerase γ, eukaryotic polymerase δ, eukaryotic polymerase ε, eukaryotic polymerase η, eukaryotic polymerase ζ, eukaryotic polymerase ι, eukaryotic polymerase κ, *E. coli* DNA polymerase I, *E. coli* DNA polymerase III alpha subunit, *E. coli* DNA polymerase III epsilon subunits, *E. coli* polymerase IV, *E. coli* polymerase V, *T. aquaticus* DNA polymerase I, *B. stearothermophilus* DNA polymerase I, a *Euryarchaeota* polymerase, terminal deoxynucleotidyl transferase (TdT), *S. cerevisiae* polymerase 4, a translesion synthesis polymerase, reverse transcriptase, a thermostable polymerase, a telomerase, or any combination thereof.

The first protein can comprise an RNA-binding domain, a DNA-binding domain, a transactivation domain, a nuclear receptor ligand binding domain, or any combination thereof. The DNA-binding domain and/or RNA-biding domain can comprise dCas9, Gal4, hypoxia inducible factor (HIF), HIFla, cyclic AMP response element binding (CREB) protein, LexA, rtTA, an endonuclease, a zinc finger binding domain, a transcription factor, portions thereof, or any combination thereof. The transactivation domain can comprise VP16, TA2, VP64 (a tetrameric repeat of the minimal activation domain of VP16), signal transducer and activator of transcription 6 (STAT6), reticuloendotheliosis virus A oncogene (relA), TATA binding protein associated factor-1 (TAF-1), TATA binding protein associated factor-2 (TAF-2), glucocorticoid receptor TAU-1, or glucocorticoid receptor TAU-2, a steroid/thyroid hormone nuclear receptor transactivation domain, a polyglutamine transactivation domain, a basic or acidic amino acid transactivation domain, a GAL4 transactivation domain, an NF-κB transactivation domain, a p65 transactivation domain, a BP42 transactivation domain, portions thereof having transcription activating activity, or any combination thereof. The first protein can comprise Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, and any combination thereof. The first protein can comprise Cas9, Cpf1, Cas13a, or a variant or derivative thereof.

In some embodiments, the first input level correlates (e.g., positively correlates) with a first level of activation of a first signal transducer and/or a second level of activation of a second signal transducer. In some embodiments, the first output level correlates (e.g., positively correlates) with a first level of activation of a first signal transducer and/or a second level of activation of the second signal transducer. In some embodiments, the first level of activation of the first signal transducer can be related to a number of molecules of the first signal transducer in a first transducer active state, and/or wherein the second level of activation of the second signal transducer can be related to a number of molecules of the second signal transducer in a second transducer active state. In some embodiments, the synthetic protein circuit can be capable of directly or indirectly inducing cell death in the presence of the aberrant signaling of a first signal transducer, or when a first level of activation of the first signal transducer is above a first signal transducer activation threshold. In some embodiments, the substrate can comprise Caspase-3, Caspase 7, Caspase-9, Caspase-8, Bax, Bid, Bad, Bak, BCL2L11, p53, PUMA, Diablo/SMAC, S-TRAIL, or any combination thereof. The first signal transducer, the second signal transducer, or both can comprise AKT, PI3K, MAPK, p44/42 MAP kinase, TYK2, p38 MAP kinase, PKC, PKA, SAPK, ELK, INK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof.

In some embodiments, the first protein is a protein of interest. As used herein, a "protein of interest" can be any protein, including naturally-occurring and non-naturally occurring proteins. Examples of protein of interest include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof, and interferons and variants thereof.

In some embodiments, the first protein is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as -glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I 3, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the first protein comprises an active fragment of a protein, such as any of the aforementioned proteins. In some embodiments, the protein of interest is a fusion protein comprising some or all of two or more proteins. In some embodiments a fusion protein can comprise all or a portion of any of the aforementioned proteins.

In some embodiments, the first protein comprises a multi-subunit protein. For examples, the first protein can comprise two or more subunits, or two or more independent polypeptide chains. In some embodiments, the first protein can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody. In some embodiments, the protein of interest can be an antigen-binding moiety as disclosed herein.

In some embodiments, the first protein comprises a pro-survival protein (e.g., Bcl-2, Bcl-XL, Mcl-1 and A1). In some embodiments, the first protein is a apoptotic factor or apoptosis-related protein such as, for example, AIF, Apaf e.g. Apaf-1, Apaf-2, Apaf-3, oder APO-2 (L), APO-3 (L), Apopain, Bad, Bak, Bax, Bcl-2, Bcl-$x_L$, Bcl-xs, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdRl, DcRl, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, INK, Lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the first protein comprises a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1 L, TBX3b, SV40 large T, hTERT, miR-291, miR-294, miR-295, or any combinations thereof. In some embodiments, the first protein comprises a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the first protein comprises a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including Clq, MBL, Clr, Cls, C2b, Bb, D, MASP-1, MASP-2, C4b, C3b, C5a, C3a, C4a, C5b, C6, C7, C8, C9, CR1, CR2, CR3, CR4, ClqR, C1INH, C4 bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, TypIII repeat extra domain A of fibronectin; the receptors, including IL-1 RI, TLR1, TLR2, TLR3, TLR4, TLR5, TLR6, TLR7, TLR8, TLR9, TLR10, TLR11; the signal transducers including components of the Small-GTPases signaling (RhoA, Ras, Rac1, Cdc42 etc.), components of the PIP signaling (PI3K, Src-Kinases, etc.), components of the MyD88-dependent signaling (MyD88, IRAK1, IRAK2, etc.), components of the MyD88-independent signaling (TI-CAM1, TICAM2 etc.); activated transcription factors including e.g. NF-κB, c-Fos, c-Jun, c-Myc; and induced target genes including IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

The first protein in an first active state can be capable of rendering a resident cell sensitive to a prodrug. For example, in some embodiments, the first protein comprises cytosine deaminase and uracil phosphoribosyl transferase, and the prodrug is 5-fluorocytosine (5-FC). In some embodiments, the first protein comprises thymidine kinase (TK), and the prodrug comprises ganciclovir. In some embodiments, the first protein is a protein which, upon administration of a prodrug, effects transition of a gene product to a compound which kills its host cell (e.g., a suicide gene product). Any suitable suicide gene and prodrug is contemplated this disclosure, such as, for example, the suicide gene/prodrug combinations depicted in Table 1.

TABLE 1

| SUICIDE GENES AND PRODRUGS | |
|---|---|
| Suicide Gene | Prodrug(s) |
| HSV thymidine kinase (TK) | Ganciclovir (GCV); Ganciclovir elaidic acid ester; Penciclovir (PCV); Acyclovir (ACV); Valacyclovir (VCV); (E)-5-(2-bromovinyl)-2'-deoxyuridine (BVDU): Zidovuline (AZT); 2'-exo-methanocarbathymidine (MCT) |
| Cytosine Deaminase (CD) | 5-fluorocytosine (5-FC) |
| Purine nucleoside phosphorylase (PNP) | 6-methylpurine deoxyriboside (MEP); fludarabine (FAMP) |
| Cytochrome p450 enzymes (CYP) | Cyclophosphamide (CPA); Ifosfamide (IFO); 4-ipomeanol (4-IM) |
| Carboxypeptidases (CP) | 4-[(2-chloroethyl)(2-mesyloxy-ethyl)amino]benzoyl-L-glutamic acid (CMDA); Hydroxy-and amino-aniline mustards; Anthracycline glutamates; Methotrexate α-peptides (MTX-Phe) |

TABLE 1-continued

SUICIDE GENES AND PRODRUGS

| Suicide Gene | Prodrug(s) |
| --- | --- |
| Caspase-9 | AP1903 |
| Carboxylesterase (CE) | Irinotecan (IRT); Anthracycline acetals |
| Nitroreductase (NTR) | dinitroaziridinylbenzamide CB1954; dinitrobenzamide mustard SN23862; 4-Nitrobenzylcarbamates; Quinones |
| Horse radish peroxidase (HRP) | Indole-3-acetic acid (IAA); 5-Fluoroindole-3-acetic acid (FIAA) |
| Guanine Ribosyltransferase (XGRTP) | 6-Thioxanthine (6-TX) |
| Glycosidase enzymes | HM1826; Anthracycline acetals |
| Methionine-α,γ-lyase (MET) | Selenomethionine (SeMET) |
| Thymidine phosphorylase (TP) | 5'-Deoxy-5-fluorouridine (5'-DFU) |

The third polypeptide domain and the second polypeptide domain can be capable of associating with each other to constitute a first protein capable of being in a first protein inactive state when the third partner domain binds the second partner domain. The third polypeptide domain and the second polypeptide domain can be capable of associating with each other to constitute a first protein capable of being in a first protein dominant negative state when the third partner domain binds the second partner domain. The first protein in a first protein dominant negative state can be capable of reducing or preventing the first enzymatic reaction. The third polypeptide domain can comprise less than 50% homology to the first polypeptide domain. The third polypeptide domain can be a variant of the first polypeptide domain. In some embodiments, the sequence identity between the first polypeptide domain and the third polypeptide domain can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the sequence identity between the first polypeptide domain and the third polypeptide domain can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 270%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Thresholding Protein Signals

Disclosed herein include methods of thresholding protein signals. In some embodiments, the method comprises expressing a synthetic protein circuit disclosed herein in a cell. Disclosed herein include methods of modulating the threshold concentration of an input species needed to generate a output protein species. In some embodiments, the method comprises expressing a synthetic protein circuit disclosed herein in a cell. Disclosed herein include methods of modulating a threshold first input level. In some embodiments, the method comprises expressing a synthetic protein circuit disclosed herein in a cell. Disclosed herein include methods of modulating a threshold second input polypeptide concentration. In some embodiments, the method comprises expressing a synthetic protein circuit disclosed herein in a cell. In some embodiments, the compositions and methods provided herein increase the threshold concentration of an input species needed to generate a output protein species. In some embodiments, the compositions and methods provided herein decrease the threshold concentration of an input species needed to generate a output protein species. In some embodiments, the compositions and methods provided herein increase the first input level needed to generate an thresholding output. In some embodiments, the compositions and methods provided herein decrease the first input level needed to generate an thresholding output.

In some embodiments, a thresholding output level is related to a number of molecules of the first protein in a first protein active state. In some embodiments, a thresholding output level is related to a number of molecules of the first product. In some embodiments, the thresholding output is generated in response to a first input. In some embodiments, a first output is generated in response to the first input, wherein a first output level correlates (e.g., positively correlates) with a first input level. In some embodiments, the thresholding output is generated in response to the first output. In some embodiments, the first output modulates the localization of second input polypeptide, the generation of the second input polypeptide, the stability of the second input polypeptide, and/or the second input polypeptide concentration. In some embodiments, the generation of the second input polypeptide, the stability of the second input polypeptide, the activity of the second input polypeptide, and/or the second input polypeptide concentration correlates (e.g., positively correlates) with the first output level and/or the first input level.

A precursor second input polypeptide can comprise a first cut site. The first polypeptide domain and the second polypeptide domain can be incapable of associating with each other to constitute a first protein capable of being in a first protein active state when the first cut site is intact.

The first output can comprise a first protease in a first protease active state. The first output level can be related to a number of molecules of the first protease in a first protease active state. The first output can comprise the first protease in the first protease active state cutting the first cut site of the precursor second input polypeptide, thereby generating the second input polypeptide.

In some embodiments, no thresholding output is generated below a threshold first input level. In some embodiments, the thresholding output level generated below a threshold first input level is less than about 10% (e.g., 0%, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, or a number or a range between any two of these values) as compared to the thresholding output level generated at or above the threshold first input level. In some embodiments, the threshold first input level in the absence of the thresholding input polypeptide is a basal threshold first input level. In some embodiments, the threshold first input level in the presence of a first thresholding polypeptide concentration and in the presence of a first tuner polypeptide concentration is a first threshold first input level. In some embodiments, the threshold first input level in the presence of a first thresholding polypeptide concentration and in the presence of a second tuner polypeptide concentration is a second threshold first input level. In some embodiments, the threshold first input level in the presence of a second thresholding polypeptide concentration and in the presence of a first tuner polypeptide concentration is a third threshold first input level. The first threshold first input level, the second threshold first input level, and/or the third threshold first input level can be at least about 10% (e.g., 2%, 3%, 4%, 5%, 6%, 7%, 8%, 9%, 10%, 11%, 12%, 13%, 14%, 15%, 16%, 17%, 18%, 1$^9$%, 20%, 25%, 30%, 40%, 50%, 75%, 100%, 150%, 200%, 300%, 400%, 500%, 1000%, or higher and overlapping ranges therein) higher than the basal threshold first input level.

In some embodiments, no thresholding output is generated below a threshold second input polypeptide concentration. The thresholding output level generated below a threshold second input polypeptide concentration can be less than about 10% (e.g., 0%, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, or a number or a range between any two of these values) as compared to the thresholding output level generated at or above the threshold second input polypeptide concentration. In some embodiments, the threshold second input polypeptide concentration in the absence of the thresholding input polypeptide is a basal threshold second input polypeptide concentration. In some embodiments, the threshold second input polypeptide concentration in the presence of a first thresholding polypeptide concentration and in the presence of a first tuner polypeptide concentration is a first threshold second input polypeptide concentration. In some embodiments, the threshold second input polypeptide concentration in the presence of a first thresholding polypeptide concentration and in the presence of a second tuner polypeptide concentration is a second threshold second input polypeptide concentration. The threshold second input polypeptide concentration in the presence of a second thresholding polypeptide concentration and in the presence of a first tuner polypeptide concentration is a third threshold second input polypeptide concentration. The first threshold second input polypeptide concentration, the second threshold second input polypeptide concentration, and/or the third threshold second input polypeptide concentration can be at least about 10% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 300%, 400%, 500%, 1000%, or higher and overlapping ranges therein) higher than the basal threshold second input polypeptide concentration.

The second tuner polypeptide concentration can be at least about 10% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) higher than the first tuner polypeptide concentration. The second thresholding polypeptide concentration can be at least about 10% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) higher than the first thresholding polypeptide concentration.

Methods of Treatment

Disclosed herein include methods of treating a disease or disorder. In some embodiments, the method comprises expressing a synthetic protein circuit disclosed herein in a cell of a subject in need thereof. In some embodiments, the disease or disorder is characterized by an aberrant signaling of one or more signal transducers. Many diseases and disorders are caused by aberrant signaling of one or more signal transducers. For example, many oncogenic mutations are activating mutations in growth-promoting signal transducers. Methods to selectively kill or inactivate cells with oncogenic mutations could provide therapeutic strategies for cancer treatment. The disease or disorder can be characterized by an aberrant signaling of a first transducer and/or an aberrant signaling of a second transducer, wherein the first transducer and the second transducer can be identical or different. The disease or disorder can be characterized by an aberrant signaling of a RAS protein. The disease or disorder can be a cancer. The disease or disorder can comprise a RASopathy (e.g., Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, Legius syndrome, or any combination thereof). The disease can comprise a neurological disease or a neurodegenerative disease. The disease can comprise an autoimmune disease and/or an infectious disease. In some embodiments, the method comprises administering a prodrug. The prodrug can comprise 5-fluorocytosine (5-FC), ganciclovir, or any of the prodrugs listed in Table 1. The disease or disorder can be characterized by an aberrant signaling of the first transducer, such as those described herein at Tables 1-3 of U.S. application Ser. No. 16/556,063, filed on Aug. 29, 2019, the content of which is incorporated herein by reference in its entirety. In some embodiments, aberrant signaling of the one or more signal transducers is a direct or indirect cause of the disease or disorder. In some embodiments, aberrant signaling of the one or more signal transducers is a direct or indirect cause of a symptom of the disease or disorder. In some embodiments of the methods provided herein, treatment reduces the aberrant signaling of the one or more signal transducers. In some embodiments of the methods provided herein, treatment reduces the induces the death of cells comprising the aberrant signaling of the one or more signal transducers. In some embodiments of the methods provided herein, treatment reduces the induces or prevents an immune response versus cells comprising the aberrant signaling of the one or more signal transducers. In some embodiments, treatment of the disease or disorder comprises the action of a thresholding output (e.g., a first enzymatic reaction, a first protein in a first protein in a first protein active state) as described herein.

In some embodiments, aberrant signaling refers to a measurable or observable change in the level of activity of a signal transducer which is associated with a disease or disorder (e.g., with susceptibility, onset, or progression of a cancer). Aberrant signaling can comprise any level of activity that is statistically significant different from the expected (e.g., normal or baseline) level of activity of the signal transducer. Aberrant signaling can comprise a level of activity of a signal transducer that is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) increased or decreased as compared to a normal tissue sample and/or prior tissue sample. Aberrant signaling can comprise a level of activity of a signal transducer that is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) increased or decreased an analogous sample from a portion of a subject not having a disorder or disorder characterized by aberrant signaling. Aberrant signaling can comprise a level of activity of a signal transducer that is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) increased or decreased as compared a control. Aberrant signaling can comprise a change in signaling activity as compared a control. As used herein the term "control" can refer to predetermined values, and also refers to samples of materials tested in parallel with the experimental materials. Examples include samples from control populations, biopsy samples taken from tissue adjacent to a biopsy sample suspected of being in a disease state (e.g., cancerous) and control samples generated through manufacture to be tested in parallel with the experimental samples. As used herein the term "control" includes positive and negative controls which may be a predetermined value that can take a variety of forms. The control(s) can be a single cut-off value, such as a median or mean, or can be established based upon comparative groups, such as in groups having a normal level of activity of the signal transducer and groups having an abnormal level of activity of the signal transducer. Another example of a comparative group is a group having a particular disease or disorder characterized by an aberrant signaling of the signal transducer, and a group without the disease or disorder characterized by an aberrant signaling of the signal transducer. The predetermined value of a control will depend upon the particular population selected. For example, an apparently healthy population will have a different level of activity of a given signal transducer than will a population which is known to have a particular disease or disorder characterized by an aberrant signaling of the signal transducer. Accordingly, the predetermined value selected may take into account the category in which an individual falls. Appropriate ranges and categories can be selected with no more than routine experimentation by those of skill in the art. Typically the control will be based on apparently healthy individuals in an appropriate age bracket. As used herein, the term "aberrant signaling" can include a higher or lower level of activity of a signal transducer relative to a selected control.

Aberrant signaling can comprise an active signal transducer repressor and an active signal transducer. Aberrant signaling can comprise an inactive signal transducer activator and an active signal transducer. Aberrant signaling can comprise an inactive signal transducer. Aberrant signaling can comprise an underactive signal transducer. Aberrant signaling can comprise a constitutively inactive signal transducer over a period of time. Aberrant signaling can comprise an inactive signal transducer repressor and an inactive signal transducer. Aberrant signaling can comprise an active signal transducer activator and an inactive signal transducer. Aberrant signaling can comprise an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

The synthetic protein circuit can be capable of directly or indirectly inducing cell death in the presence of the aberrant signaling. In some embodiments, the thresholding output directly or indirectly induces cell death in the presence of aberrant signaling. In some embodiments, the synthetic protein circuit directly or indirectly induces cell death when a first level of activation of the first signal transducer is above a first signal transducer activation threshold and/or a second level of activation of the second signal transducer is below a second signal transducer activation threshold. In some embodiments, the thresholding output directly or indirectly induces cell death when a first level of activation of the first signal transducer is above a first signal transducer activation threshold and/or a second level of activation of the second signal transducer is below a second signal transducer activation threshold.

The administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. There are provided, in some embodiments, pharmaceutical composition for administration of any of the compositions provided herein. The pharmaceutical composition can be formulated with a pharmaceutically acceptable carrier or excipient. A pharmaceutically acceptable carrier or excipient refers to a carrier (e.g., carrier, media, diluent, solvent, vehicle, etc.) which does not significantly interfere with the biological activity or effectiveness of the active ingredient(s) of a pharmaceutical composition and which is not excessively toxic to the host at the concentrations at which it is used or administered. Other pharmaceutically acceptable ingredients can be present in the composition as well. Suitable substances and their use for the formulation of pharmaceutically active compounds are well known in the art. A pharmaceutical composition is typically formulated to be compatible with its intended route of administration. For topical application, a pharmaceutical composition may be formulated in a suitable ointment, lotion, gel, or cream containing the active components suspended or dissolved in one or more pharmaceutically acceptable carriers suitable for use in such compositions. For some applications, the composition is formulated as a solid (e.g., lyophilized), liquid, gel, or hydrogel and may contain additives such as surfactants, buffers (e.g., succinate), salts (e.g., sodium chloride), polymers (e.g., polysaccharides, hyaluronic acid), proteins (e.g., albumin, human serum albumin), or amino acids (e.g., methionine).

Nucleic Acids

Disclosed herein include nucleic acids encoding a synthetic protein circuit provided herein. In some embodiments, the nucleic acid encodes a synthetic protein circuit comprising: a first input polypeptide comprising a first partner domain and a first polypeptide domain; a second input polypeptide comprising a second partner domain and a second polypeptide domain, wherein the first partner domain is capable of binding the second partner domain, wherein the first polypeptide domain and the second polypeptide domain are capable of associating with each other to constitute a first protein capable of being in a first protein active state when the first partner domain binds the second partner domain; and a thresholding polypeptide comprising a third partner domain and a third polypeptide domain, wherein the third partner domain is capable of binding the second partner domain, wherein the first protein is not in the first protein active state when the third partner domain binds the second partner domain. In some embodiments, the nucleic acid encodes a synthetic protein circuit comprising: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the first input polypeptide and the third input polypeptide are in close proximity. In some embodiments, the nucleic acid encodes a synthetic protein circuit comprising: a first input polypeptide comprising a first partner domain and a first polypeptide domain; a second input polypeptide comprising a second partner domain and a second polypeptide domain, wherein the first input polypeptide and the second input polypeptide have weak association affinity, and wherein the first polypeptide domain and the second polypeptide domain are capable of associating with each other to constitute a first protein capable of being in a first protein active state when the first input polypeptide and the second input polypeptide are in close proximity; a thresholding polypeptide comprising a third partner domain and a third polypeptide domain, wherein the first protein is not in the first protein active state when the second input polypeptide and the third input polypeptide are in close proximity The nucleic acid can comprise at least one regulatory element for expression of the synthetic protein circuit. The nucleic acid can comprise a vector, such as any of the viral vectors described in U.S. application Ser. No. 16/555,604, filed on Aug. 29, 2019, the content of which is incorporated herein by reference in its entirety. In some embodiments, the vector can comprise an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector can comprise an RNA viral vector. In some embodiments, the vector can be derived from one or more negative-strand RNA viruses of the order Mononegavirales. In some embodiments, the vector can be a rabies viral vector. Many such vectors useful for transferring exogenous genes into target mammalian cells are available. The vectors may be episomal, e.g. plasmids, virus-derived vectors such cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Retroviral vectors can be "defective", i.e. unable to produce viral proteins required for productive infection. Replication of the vector can require growth in the packaging cell line. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., a synthetic protein circuit component) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector. One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector. Other non-integrative viral vectors contemplated herein are single-strand negative-sense RNA viral vectors, such Sendai viral vector and rabies viral vector. Another example of a non-integrative vector is a minicircle vector. Minicircle vectors are circularized vectors in which the plasmid backbone has been released leaving only the eukaryotic promoter and cDNA(s) that are to be expressed. As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of nonessential viral genes. The vector and/or particle may be utilized for the purpose of transferring nucleic acids into cells either in vitro or in vivo. Numerous forms of viral vectors are known in the art.

In some embodiment, the vectors can include a regulatory sequence that allows, for example, the translation of multiple proteins from a single mRNA. Non-limiting examples of such regulatory sequences include internal ribosome entry site (TRES) and 2A self-processing sequence. In some embodiments, the 2A sequence is a 2A peptide site from foot-and-mouth disease virus (F2A sequence). In some embodiments, the F2A sequence has a standard furin cleavage site. In some embodiments, the vector can also comprise regulatory control elements known to one of skill in the art to influence the expression of the RNA and/or protein products encoded by the polynucleotide within desired cells of the subject. In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an ration and the splice donor and splice acceptor sequences that regulate the splicing of said intron. Another example of a regulatory element is a transcription termination signal and/or a polyadenylation sequence.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF 1 alpha; or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide m response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present: the greater the amount of signal or stimuli, the greater the increase or decrease in expression.

The first input polypeptide, the second input polypeptide, the thresholding polypeptide, and/or the tuner polypeptide can be encoded on a single open reading frame, and wherein two or more of first input polypeptide, the second input polypeptide, the thresholding polypeptide, and/or the tuner polypeptide can be separated by one or more self-cleaving peptides. The first input polypeptide, the second input polypeptide, the thresholding polypeptide, and/or the tuner polypeptide can be encoded on a single transcript, and wherein translations of the first input polypeptide, the second input polypeptide, the thresholding polypeptide, and/or the tuner polypeptide can be each driven by a separate internal ribosome entry site. The sequences of the internal ribosome entry sites can be identical or different.

EXAMPLES

Some aspects of the embodiments discussed above are disclosed in further detail in the following examples, which are not in any way intended to limit the scope of the present disclosure.

Example 1

Split Inteins and Non-Productive Splicing can Provide Molecular Titration of Protease Activity This example provides validation for the threshold circuit design concept described herein by showing that the Cfa split intein system can be used to create a thresholding effect with protease activity as an output. In some embodiments, the thresholding module design is based on the Cfa split intein system. Cfa provides modular domains that can undergo reversible protein dimerization and irreversible protein splicing (Stevens et al, JACS 2016). The Cfa intein has two separate translated polypeptides, CfaN and CfaC. When fused with extein protein domains, CfaN and CfaC can reversibly dimerize. In the dimeric form, the CfaN and CfaC can irreversibly excise themselves and thereby splice the exteins together to form a single spliced protein (depicted in FIGS. 3A-3B). A truncated variant of CfaN, CfaN2, lacks an essential domain for irreversible protein splicing, but can still reversibly dimerize with CfaC, (Stevens et al, JACS 2016).

To create the input protein activity, CfaN2 and CfaC were fused to each half of a split Tobacco Vein Mottling Virus (TVMV) protease, denoted TVMVP. The resulting proteins, nTVMVP-CfaN2 (SEQ ID NO: 3) and CfaC-cTVMVP (SEQ ID NO: 2), function as protein-level inputs to the system. Dimerization of CfaN2 and CfaC can bring two halves of TVMVP together to reconstitute TVMVP activity (depicted in FIGS. 3A-3B).

Figure 3A:
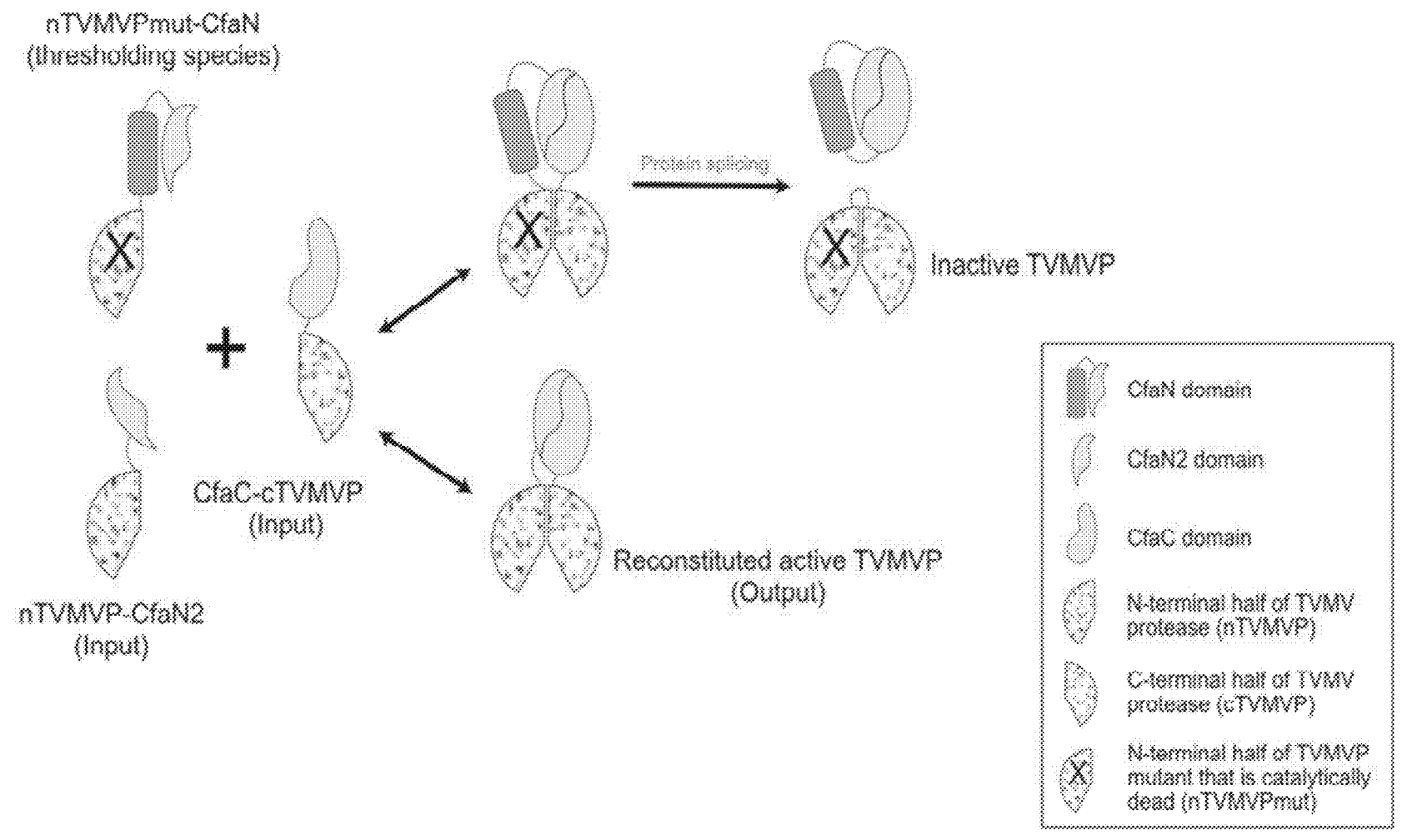
Figure 3B:
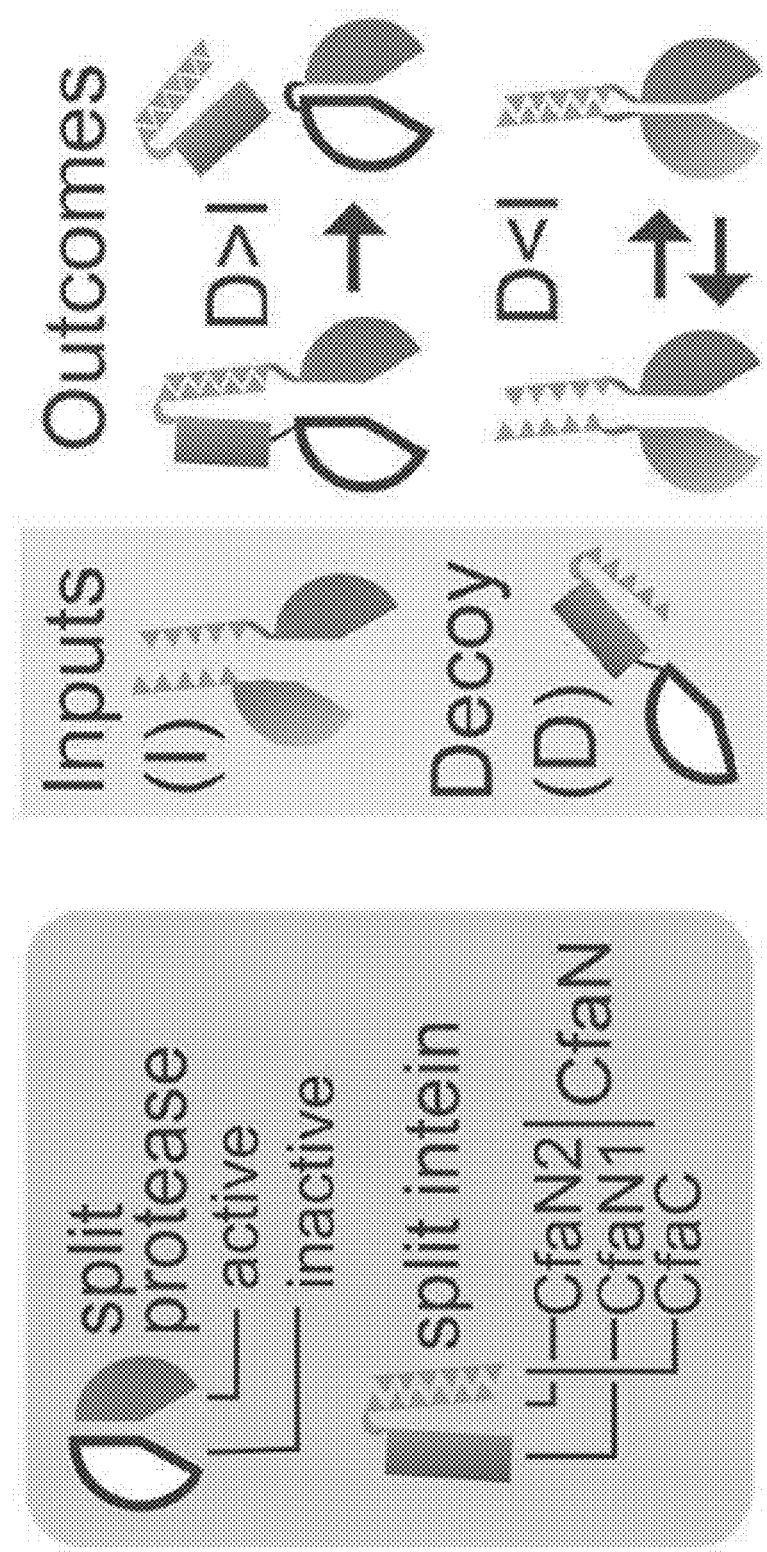

To introduce a thresholding effect, a third species (e.g., a decoy) was engineered by fusing CfaN with the N-terminal half of a catalytically dead TVMVP mutant, nTVMVPmut-CfaN (SEQ ID NO: 1). This component can undergo irreversible protein splicing with CfaC-cTVMVP to form a catalytically inactive TVMVP (depicted in FIGS. 3A-3B). The irreversibility of this reaction can provide a flux of input protein into inactive components that do not further affect the system. In this way, the thresholding species (nTVMVPmut-CfaN) and part of the input (CfaC-cTVMVP) can mutually annihilate one another, approximately subtracting a fixed amount of one input species (CfaC-cTVMVP), and thereby introducing a thresholding effect into the system whose magnitude can be controlled by modulating the concentration or expression of nTVMVPmut-CfaN (FIGS. 3A-3B).

Figures 3C, 3D:
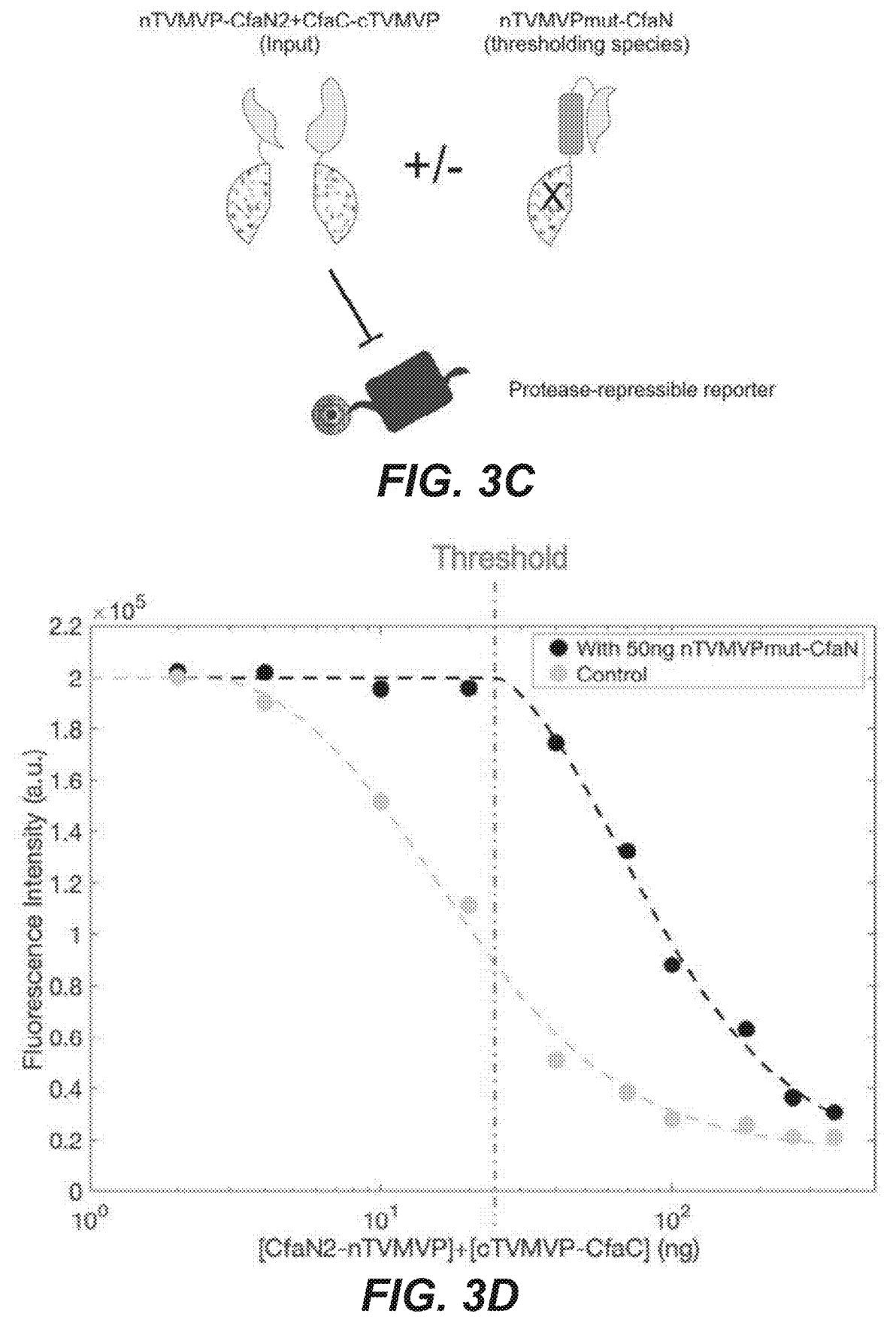
Figure 3E:
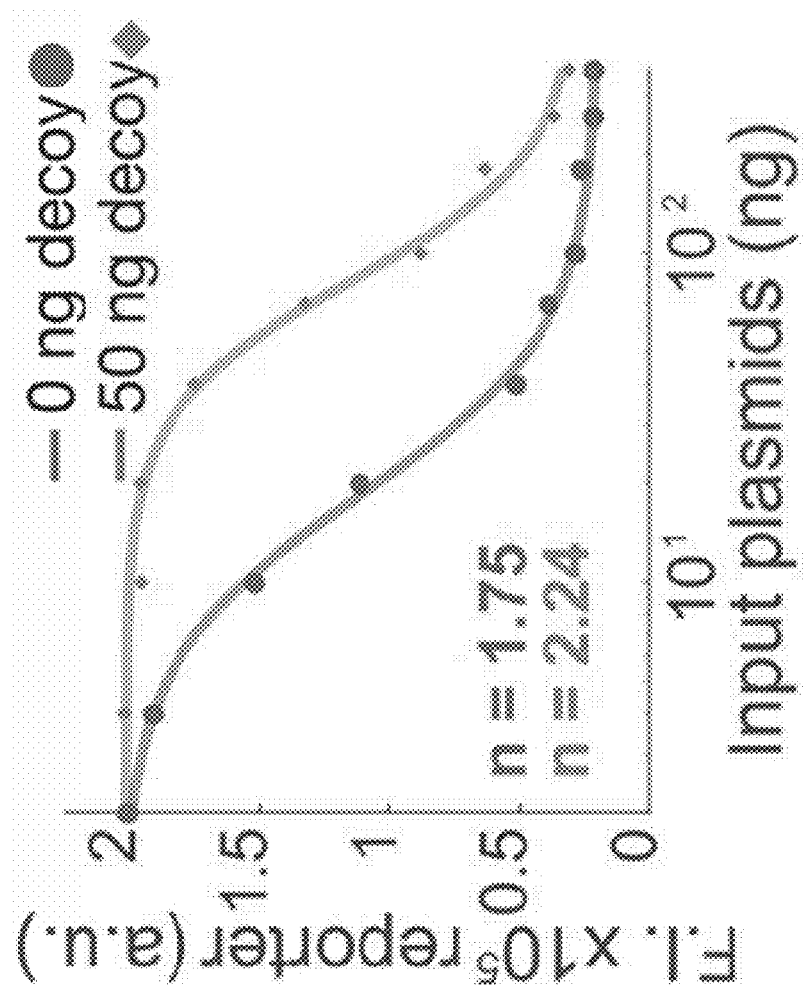

To experimentally test the threshold circuit design, a protease-repressible fluorescence reporter (X. Gao, et al, Science 2018) was utilized to read out the concentration of active TVMVP as a function of input levels (FIG. 3C). With this reporter, fluorescence intensity decreases with increasing TVMV protease activity. Different amounts of input plasmids expressing nTVMVP-CfaN2 and CfaC-cTVMVP were transfected together with 50 ng of the thresholding species plasmid expressing nTVMVPmut-CfaN into HEK293T cells stably the expressing protease-repressible reporter. As a negative control, input plasmids were transfected together with 50 ng of an empty plasmid. Flow cytometry was used to quantify the fluorescence intensity of transfected cells 48 hr after transfection. Compared with the control group, protease activity in the experimental group was fully inhibited under low input concentrations, and began to increase only when input concentrations crossed a threshold, at approximately 20 ng, as designed. This result shows that the thresholding module can operate in HEK293T cells (FIGS. 3D-3E).

Figures 3F, 3G:
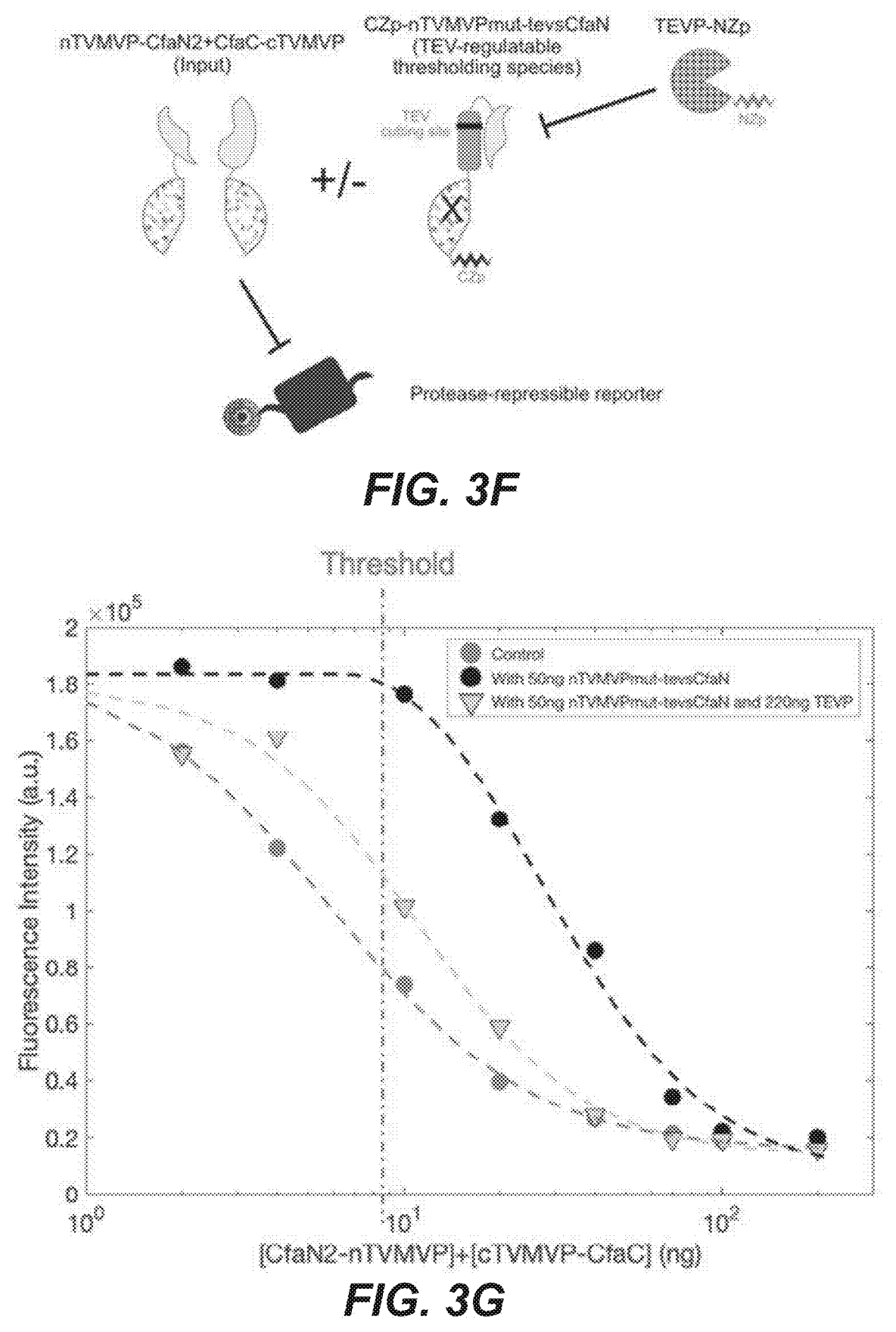

The thresholding module can be further regulated by an additional protein-level input. A TEV protease cleavage site was introduced into the CfaN domain. With this design, adding TEV protease can disrupt the CfaN domain in the thresholding species, thereby reducing the threshold level. To ensure efficient TEVP cleavage, CZp and NZp, a pair of interacting leucine zippers, were fused to nTVMVPmut-tevsCfaN and TEVP, respectively (FIG. 3F). The resulting constructs were a TEV-regulatable thresholding species (SEQ ID NO: 4; SEQ ID NO: 5 represents a variant) and an TEV-NZp protease (SEQ ID NO: 6). As expected, the TEV-regulatable thresholding species maintained its thresholding capability in the absence of TEV protease. However, its thresholding effects were strongly reduced by addition of TEVP (FIG. 3G). This result shows that it is possible use other proteases to tune or modulate the effects of the thresholding module.

Example 2

Threshold Design is Modular for Other Split Proteins

Figure 4A:
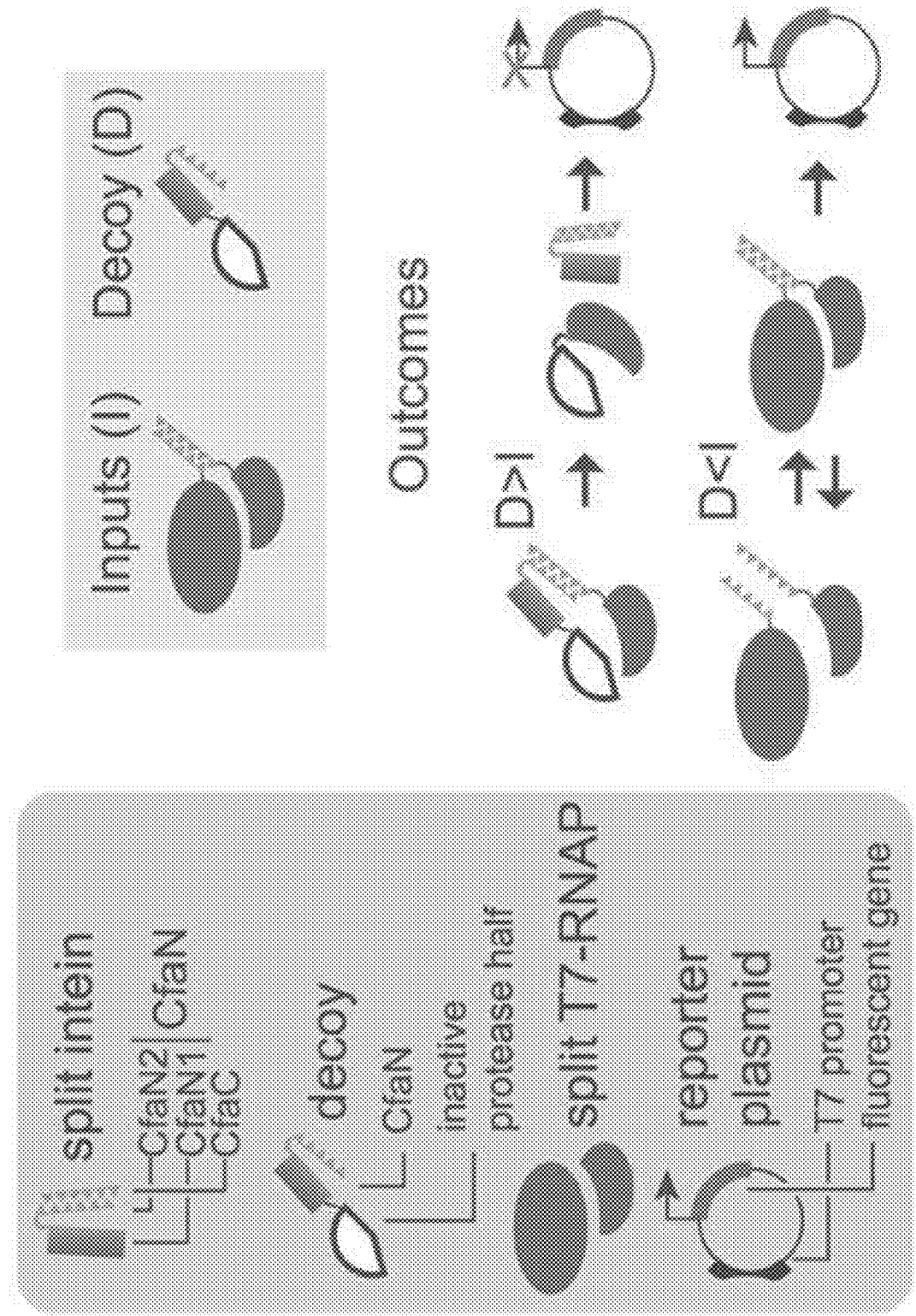
FIG. 4A depicts the design of a synthetic protein circuit creating a thresholding effect on split T7 RNA polymerase activity.
Figure 4B:
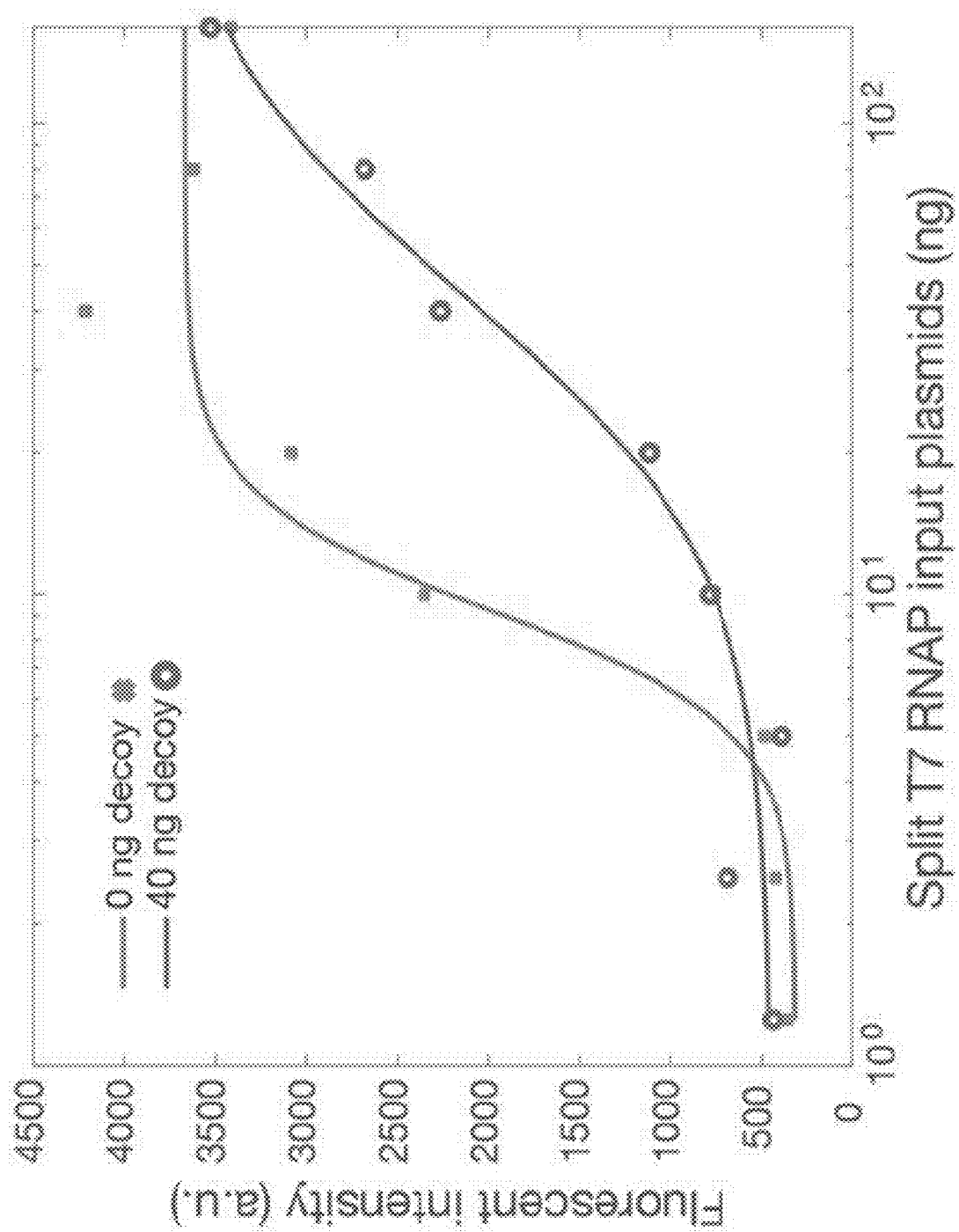
FIG. 4B depicts data related to a thresholding effect on split T7 RNA polymerase activity by the synthetic protein circuit depicted in FIG. 4A.

This example provides further validation for the threshold circuit design concept described herein by showing that the same Cfa split intein system described in Example 1 can be used to create a thresholding effect on split T7 RNA polymerase activity. In this design, CfaN2 and CfaC were fused to each half of a split T7-RNAP (Pu, Jinyue et al., 2017), denoted T7-RNAP (FIG. 4A). The resulting proteins, nT7RNAP-CfaN2 and CfaC-cT7RNAP, function as protein-level inputs to the system. Dimerization of CfaN2 and CfaC can reconstitute T7RNAP activity. To introduce a thresholding effect, the same third species (e.g., a decoy) employed in Example 1 where CfaN was fused to the N-terminal half of a catalytically dead TVMVP mutant, nTVMVPmut-CfaN, was used. This component can undergo irreversible protein splicing with CfaC-cT7RNAP to form a catalytically inactive T7RNAP. To experimentally test this design a T7RNAP reporter was used in which a mCherry expression is under the control of a T7 promoter. An TRES sequence was placed before the mCherry gene to permit translation in mammalian cells (FIG. 4A). Different amounts of input plasmids were transfected into HEK293T cells with 150 ng of the reporter plasmid. As a negative control, input plasmids were transfected together with 40 ng of an empty plasmid. Flow cytometry was used to quantify the fluorescence intensity of transfected cells 48 hr after transfection. Compared with the control group, T7RNAP activity in the experimental group was fully inhibited under low input concentrations, and began to increase only when input concentrations crossed a threshold, at approximately 20 ng (FIG. 4B). These results demonstrate that the design principle provided herein can be generalized to different thresholding outputs.

Example 3

CfaN2 and CfaC Domains Reconstitute Split Cas9

Figure 5A:
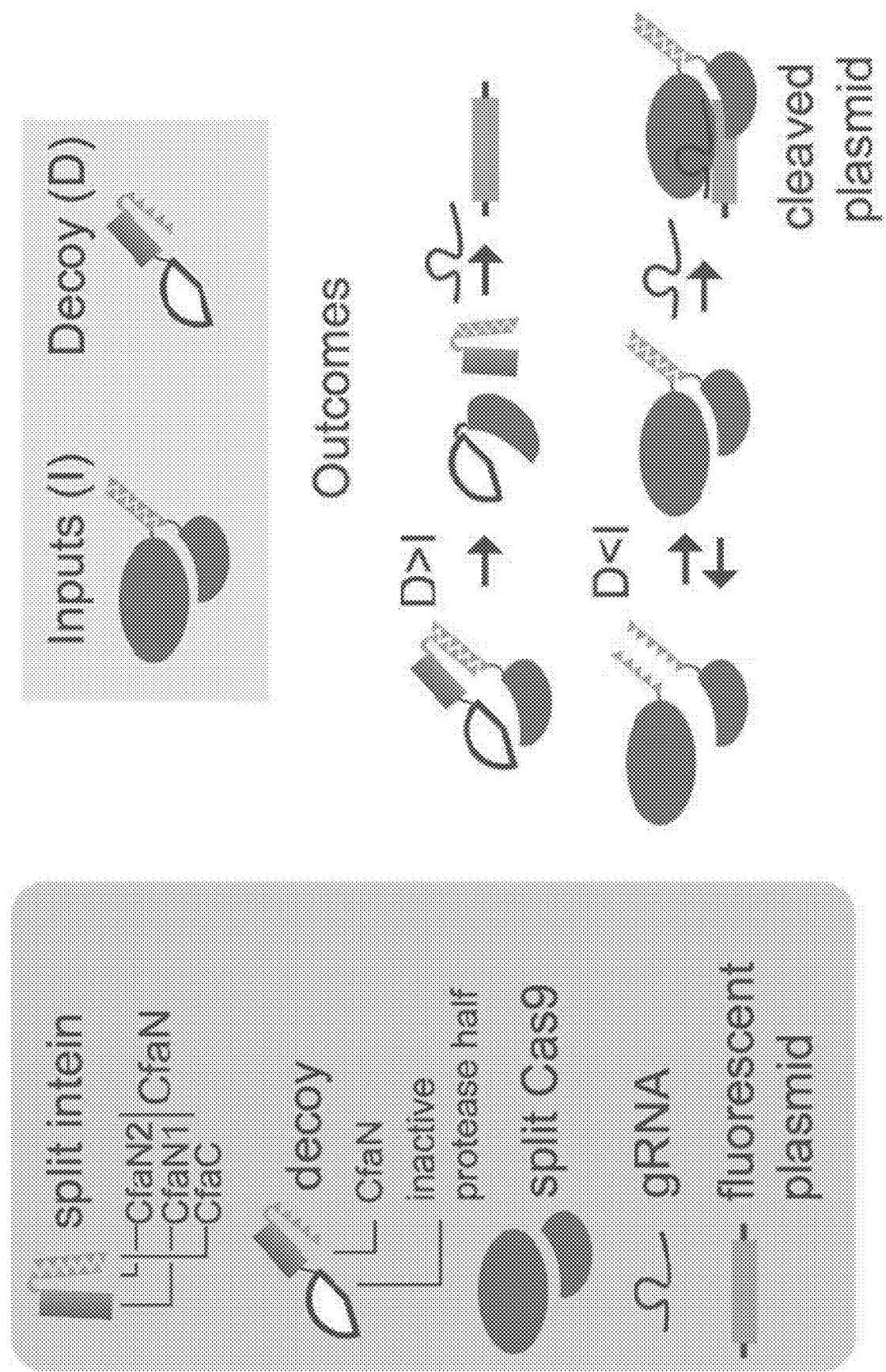
FIG. 5A depicts the design of a synthetic protein circuit creating a thresholding effect on split Cas9 activity.
Figure 5B:
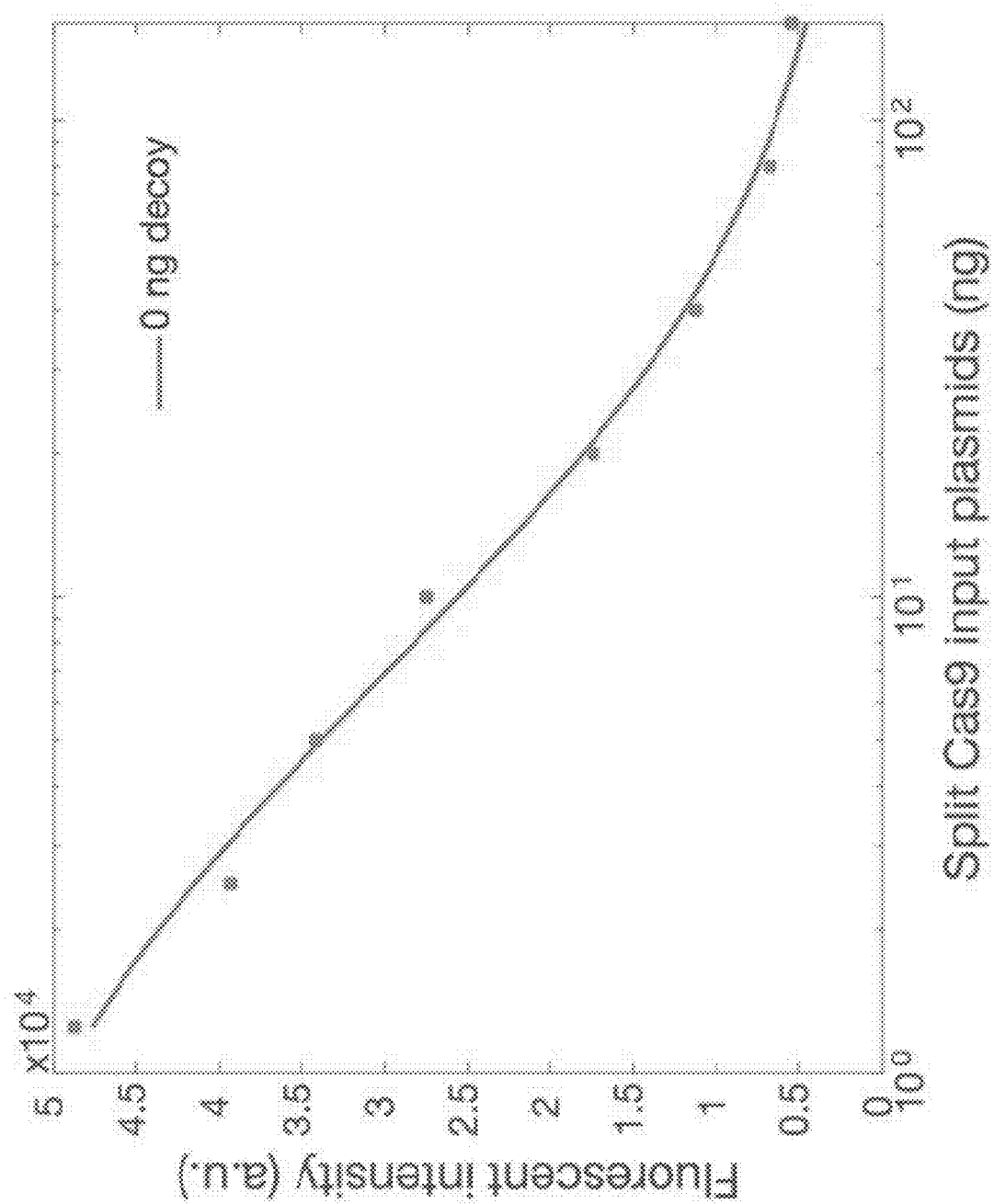
FIG. 5B depicts data related to a thresholding effect on split Cas9 activity by the synthetic protein circuit depicted in FIG. 5A.

This example provides further validation for the threshold circuit design concept described herein by showing that the same Cfa split intein system described in Example 1 can be used to reconstitute split Cas9 activity. As an initial step towards developing a thresholded split Cas9, CfaN2 and CfaC were fused to each half of a split Cas9, denoted Cas9 (FIG. 5A). The resulting proteins, nCas9-CfaN2 and CfaC-cCas9, function as protein-level inputs to the system. Dimerization of CfaN2 and CfaC reconstitute Cas9 activity. To knowledge of Applicant this is the first demonstration that part of an intein domain, specifically CfaN2 with CfaC, can be used to reconstitute Cas9 activity. To experimentally test this design a plasmid was employed expressing Citrine and a guide-RNA targeting the coding sequence of Citrine. Active Cas9 can cleave the Citrine plasmid resulting in no fluorescence (FIG. 5A). Different amounts of input plasmids were transfected into HEK293T cells with 150 ng of the reporter plasmid and 300 ng of gRNA. Flow cytometry was used to quantify the fluorescence intensity of transfected cells 48 hrs after transfection. Cas9 activity increased with increase in input plasmid concentrations (FIG. 5B). The addition of high amounts of thresholding decoy (not depicted) overwhelmed the system and must be titrated down to see effect. These results demonstrate that the design principle provided herein can be generalized to different thresholding outputs.

Example 4

Figure 6A:
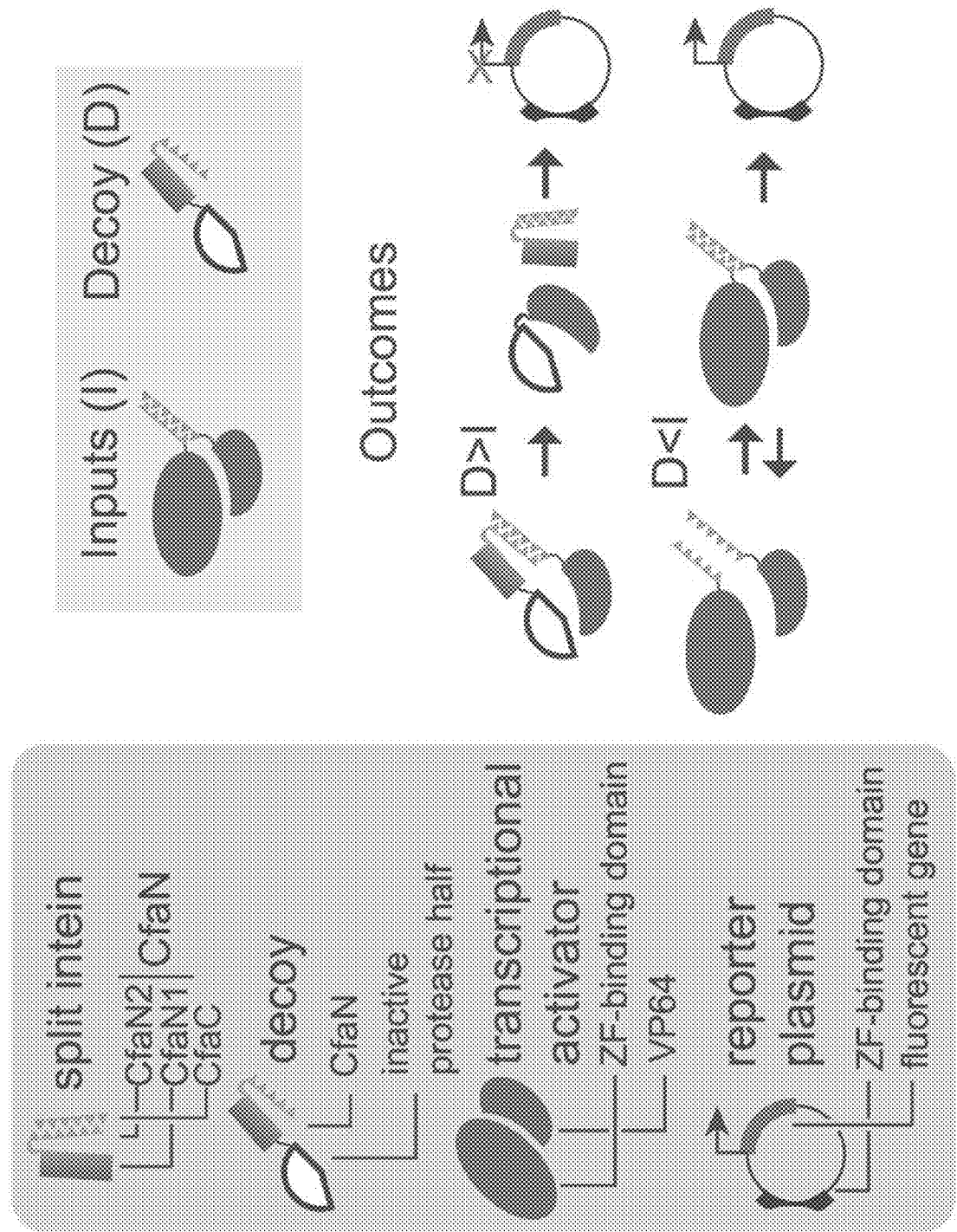
FIG. 6A depicts the design of a synthetic protein circuit creating a thresholding effect on reconstitution of two effector proteins required for trans-activation.
Figure 6B:
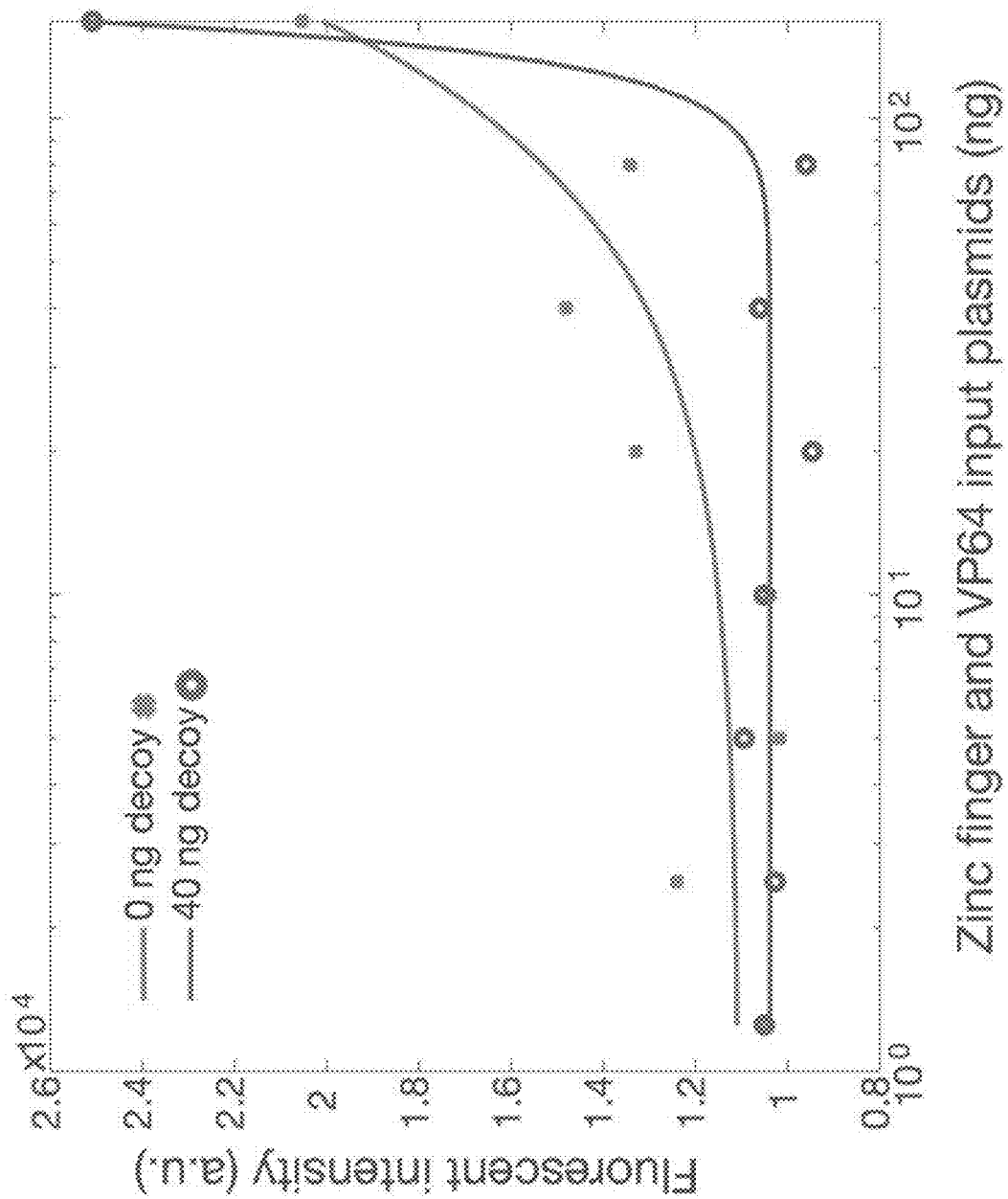
FIG. 6B depicts data related to a thresholding effect on reconstitution of two effector proteins required for trans-activation by the synthetic protein circuit depicted in FIG. 6A.

Trans-Activation with Zinc Finger and VP64 Shows Separate Proteins can be Reconstituted and Thresholded This example provides further validation for the threshold circuit design concept described herein by showing that the same Cfa split intein system described in Example 1 can be used to create a thresholding effect on reconstitution of two effector proteins required for trans-activation. In this design, CfaN2 and CfaC were fused to two different proteins, a zinc-finger (ZF) DNA-binding protein and VP64, of which dimerization of these two proteins are required for transactivation of a target gene. The resulting proteins, ZF-CfaN2 and CfaC-VP64, can function as protein-level inputs to the system (FIG. 6A). Dimerization of CfaN2 and CfaC can reconstitute gene transactivation activity. To introduce a thresholding effect, the same third species (e.g., a decoy) was used where CfaN was fused to the N-terminal half of a catalytically dead TVMVP mutant, nTVMVPmut-CfaN. This component can undergo irreversible protein splicing with CfaC-VP64 to inhibit gene activation. To experimentally test this design a fluorescent reporter was used in which Citrine expression is downstream of four tandem repeats of the ZF binding sequence (FIG. 6A). Different amounts of input plasmids were transfected into HEK293T cells with 150 ng of the reporter plasmid. As a negative control, input plasmids were transfected together with 40 ng of an empty plasmid. Flow cytometry was used to quantify the fluorescence intensity of transfected cells 48 hr after transfection. Compared with the control group, ZF-VP64 activity in the experimental group was fully inhibited under low input concentrations, and began to increase only when input concentrations crossed a threshold, at approximately 80 ng (FIG. 6B). A positive control (not depicted) showed 1.5-fold higher activation. These results demonstrate that the design principle provided herein can be generalized to different thresholding outputs.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/of" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of thresholding protein signals comprising:
   expressing a synthetic protein circuit in a cell, the synthetic protein circuit comprising:
   a first input polypeptide comprising a first partner domain and a first polypeptide domain;
   a second input polypeptide comprising a second partner domain and a second polypeptide domain, wherein the first partner domain is capable of binding the second partner domain, wherein the first polypeptide domain and the second polypeptide domain are capable of associating with each other to constitute a first protein capable of being in a first protein active state when the first partner domain binds the second partner domain; and
   a thresholding polypeptide comprising a third partner domain and a third polypeptide domain, wherein the third partner domain is capable of binding the second partner domain, wherein the first protein is not in the first protein active state when the third partner domain binds the second partner domain, wherein the first protein in the first protein active state is capable of generating a thresholding output.

2. The method of claim 1, wherein the expressing comprises administering a nucleic acid encoding the synthetic protein circuit, or
   wherein the expressing comprises administering two or more nucleic acids, and wherein the two or more nucleic acids encode the synthetic protein circuit.

3. The method of claim 2, wherein the nucleic acid comprises at least one regulatory element for expression of the synthetic protein circuit.

4. The method of claim 2, wherein the nucleic acid comprises a vector,
   optionally: wherein the vector comprises an adenovirus vector, an adeno-associated virus vector, an Epstein-Barr virus vector, a Herpes virus vector, an attenuated HIV vector, a retroviral vector, a vaccinia virus vector, or any combination thereof,
   wherein the vector comprises an RNA viral vector,
   wherein the vector is derived from one or more negative-strand RNA viruses of the order Mononegavirales, and/or
   the vector is a rabies viral vector.

5. The method of claim 1, wherein
   (i) the third polypeptide domain and the second polypeptide domain are incapable of associating to form the first protein in the first protein active state,
   (ii) the third polypeptide domain and the second polypeptide domain are capable of associating with each other to constitute a first protein capable of being in a first protein inactive state when the third partner domain binds the second partner domain, or
   (iii) the third polypeptide domain and the second polypeptide domain are capable of associating with each other to constitute a first protein capable of being in a first protein dominant negative state when the third partner domain binds the second partner domain.

6. The method of claim 1, wherein the thresholding output comprises a first enzymatic reaction with a substrate generating a first product.

7. The method of claim 6, wherein the substrate comprises a nucleic acid, a protein, a lipid, or any combination thereof.

8. The method of claim 1, wherein the third partner domain and the second partner domain are capable of inducing trans-splicing of the thresholding polypeptide and second input polypeptide when the second partner domain binds the third partner domain, thereby generating a conjugate comprising the second polypeptide domain and the third polypeptide domain, optionally wherein the conjugate is not capable of being in the first protein active state.

9. The method of claim 1, wherein the first partner domain has a reduced binding affinity for the second partner domain as compared to the binding affinity of the third partner domain for the second partner domain, or
   wherein the first partner domain binds the second partner domain with a first binding affinity, wherein the third partner domain binds the second partner domain with a second binding affinity, wherein the first partner domain is a variant of the third partner domain that is configured to reduce the first binding affinity, wherein the first partner domain comprises one or more mutations as compared to the third partner domain, and wherein the one or more mutations reduce the first binding affinity by at least 10 percent as compared to the second binding affinity.

10. The method of claim 1, wherein a thresholding output level is related to a number of molecules of the first protein in the first protein active state.

11. The method of claim 6, wherein a thresholding output level is related to a number of molecules of the first product.

12. The method of claim 1, wherein the thresholding output is generated in response to a first input.

13. The method of claim 12, wherein a first output is generated in response to the first input, wherein a first output level positively correlates with a first input level and wherein the thresholding output is generated in response to the first output.

14. The method of claim 13, wherein the first output comprises a first protease in a first protease active state and wherein the first output level is related to a number of molecules of the first protease in a first protease active state.

15. The method of claim 1, wherein the thresholding output level generated below a threshold first input level is less than about 5% as compared to the thresholding output level generated at or above the threshold first input level.

16. The method of claim 1, wherein no thresholding output is generated below a threshold second input polypeptide concentration, or
   wherein the thresholding output level generated below a threshold second input polypeptide concentration is less than about 5% as compared to the thresholding output level generated at or above the threshold second input polypeptide concentration.

17. The method of claim 1, wherein the synthetic protein circuit is capable of inducing cell death in the presence of the aberrant signaling of a first signal transducer, or when a first level of activation of the first signal transducer is above a first signal transducer activation threshold.

18. A synthetic protein circuit, comprising:
a first input polypeptide comprising a first partner domain and a first polypeptide domain;
a second input polypeptide comprising a second partner domain and a second polypeptide domain, wherein the first partner domain is capable of binding the second partner domain, wherein the first polypeptide domain and the second polypeptide domain are capable of associating with each other to constitute a first protein capable of being in a first protein active state when the first partner domain binds the second partner domain; and
a thresholding polypeptide comprising a third partner domain and a third polypeptide domain, wherein the third partner domain is capable of binding the second partner domain, wherein the first protein is not in the first protein active state when the third partner domain binds the second partner domain, wherein the first protein in the first protein active state is capable of generating a thresholding output,
wherein the third partner domain and the second partner domain are capable of inducing trans-splicing of the thresholding polypeptide and second input polypeptide when the second partner domain binds the third partner domain, thereby generating a conjugate comprising the second polypeptide domain and the third polypeptide domain, optionally wherein the conjugate is not capable of being in the first protein active state.

19. The synthetic protein circuit of claim 18, wherein the first partner domain, second partner domain, and/or third partner domain comprise an intein-N, an intein-C, a fragment thereof, or any combination thereof.

20. The synthetic protein circuit of claim 18, wherein (1) the first partner domain comprises the amino acid sequence of SEQ ID NO: 9; (2) the second partner domain comprises the amino acid sequence of SEQ ID NO: 8; and/or (3) the third partner domain comprises the amino acid sequence of any one of SEQ ID NOs: 7, 10, and 11.

* * * * *